(12) United States Patent
Keyworth et al.

(10) Patent No.: US 10,030,102 B2
(45) Date of Patent: *Jul. 24, 2018

(54) CATALYSTS

(71) Applicant: Econic Technologies Ltd, London (GB)

(72) Inventors: Colin Keyworth, Hertfordshire (GB);
Andy Chapman, London (GB);
Anthony Chartoire, Cheshire (GB);
Emmalina Hollis, London (GB);
Charlotte Williams, Oxford (GB);
Michael Kember, London (GB)

(73) Assignee: ECONIC TECHNOLOGIES LTD., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,677

(22) PCT Filed: Jul. 22, 2015

(86) PCT No.: PCT/GB2015/052115
§ 371 (c)(1),
(2) Date: Jan. 20, 2017

(87) PCT Pub. No.: WO2016/012786
PCT Pub. Date: Jan. 28, 2016

(65) Prior Publication Data
US 2017/0204221 A1    Jul. 20, 2017

(30) Foreign Application Priority Data

Jul. 22, 2014  (GB) .................................. 1412986.0
Jul. 22, 2014  (GB) .................................. 1412990.2
Jul. 22, 2014  (GB) .................................. 1412992.8

(51) Int. Cl.
*C08G 59/00* (2006.01)
*C08G 64/34* (2006.01)

(52) U.S. Cl.
CPC .................................. *C08G 64/34* (2013.01)

(58) Field of Classification Search
CPC ..... C07F 15/065; C07F 11/005; C08G 65/266
See application file for complete search history.

(56) References Cited

U.S. PATENT DOCUMENTS

2013/0172524 A1* 7/2013 Farmer .................. C07F 5/069
528/405

FOREIGN PATENT DOCUMENTS

EP         1988084 A1    11/2008
WO    2009/130470 A1    10/2009
(Continued)

OTHER PUBLICATIONS

International Search Report for PCT/GB2015/052115 dated Nov. 30, 2015 (5 pages).
(Continued)

*Primary Examiner* — Shane Fang
(74) *Attorney, Agent, or Firm* — Shumaker, Loop & Kendrick, LLP

(57) ABSTRACT

The present invention relates to the field of polymerisation catalysts, and systems comprising these catalysts for polymerising carbon dioxide and an epoxide, a lactide and/or lactone, and/or an epoxide and an anhydride. The catalyst is of formula (I):

(Continued)

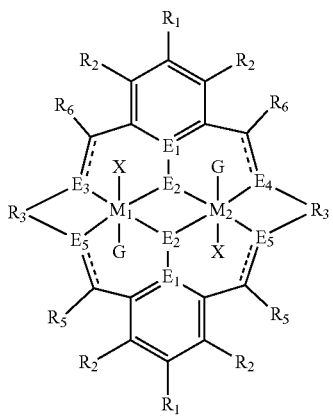

(I)

wherein at least one of $M_1$ or $M_2$ is selected from Ni(II) and Ni(III)-X. A process for the reaction of carbon dioxide with an epoxide; an epoxide and an anhydride; and/or a lactide and/or a lactone in the presence of the catalyst is also described.

53 Claims, 3 Drawing Sheets

(56) References Cited

FOREIGN PATENT DOCUMENTS

| WO | 2012/037282 A2 | 3/2012 |
|---|---|---|
| WO | 2013/007759 A1 | 1/2013 |
| WO | 2013/034750 A2 | 3/2013 |

OTHER PUBLICATIONS

P.K. Saini, C. Romain and C.K. Williams, "Dinuclear metal catalysts: improved performance of heterodinuclear mixed catalysts for CO2-epoxide copolymerization", Chem. Comm, Feb. 20, 2014, vol. 50, No. 32, pp. 4164-4167 The Royal Society of Chemistry 2014 (4 pages).

Sujit K. Dutta, et al, "Model Compounds for Iron Proteins", Inorganic Chemistry 1996, vol. 35, No. 8, 2292-2300, American Chemical Society (10 pages).

Ramprasad Das, et al., "Carboxylate Bridging of Amino Acids in Dinuclear Macrocyclic Nickel (II) Complexes", J. Chem. Soc., Dalton Trans. 1992, Issue 1., No. 7, 1253-1257 (5 pages).

Ki Ju Kim, et al., "Synthesis and Characterization of Dinuclear Ni(II) Complexes with Tetraazadiphenol Macrocycle Bearing Cyclohexanes", Bull. Korean Chem. Soc., 2006, vol. 27, No. 11, 1747-1751 (5 pages).

Yuichiro Aratake, et al., "Dinuclear nickel (II) complexes of a series of dinucleating macrocycles with similar or dissimilar coordination sites: synthesis, structure and physicochemical property", Inorganica Chimica Acta, vol. 212, No. 1-2, (1993) p. 183-190 (8 pages).

International Preliminary Report on Patentability for PCT/GB2015/052115 dated Jan. 24, 2017 (9 pages).

Nanda, K.K. et al. "Formation of Mixed Spin-state Macrocyclic dinickel (II) Complexes through Variation of Hole Size", J.Chem. Soc. Dalton Trans. pp. 2515-2520, Dec. 31, 1993.

(Abstract Only) S.J. Na et al., "Bimetallic nickel complexes of macrocyclic tetraiminodiphenols and their ethylene polymerization" J. Organometallic Chem. vol. 691, No. 4, pp. 611-620, Feb. 1, 2006.

* cited by examiner

CATALYSTS

FIELD OF THE INVENTION

The present invention relates to the field of polymerisation catalysts, and systems comprising said catalysts for polymerising carbon dioxide and an epoxide, a lactide and/or lactone, and/or an epoxide and an anhydride.

BACKGROUND

Environmental and economic concerns associated with depleting oil resources have triggered a growing interest in the chemical conversion of carbon dioxide ($CO_2$), so as to enable its use as a renewable carbon source. $CO_2$ is, despite its low reactivity, a highly attractive carbon feedstock, as it is inexpensive, virtually non-toxic, abundantly available in high purity and non-hazardous. Therefore, $CO_2$ could be a promising substitute for substances such as carbon monoxide, phosgene or other petrochemical feedstocks in many processes. One of the developing applications of $CO_2$ is copolymerization with epoxides to yield aliphatic polycarbonates. The development of effective catalysts to make such a process profitable is the subject of continuous research.

In WO2009/130470, the contents of which are incorporated herein by reference in their entirety, the copolymerisation of an epoxide with $CO_2$ using a catalyst of a class represented by formula (I) was described:

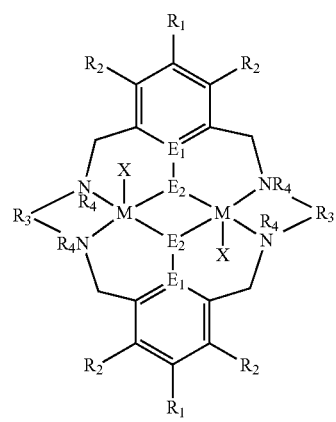

WO2013/034750, the contents of which are incorporated herein by reference in their entirety, discloses the copolymerisation of an epoxide with $CO_2$ in the presence of a chain transfer agent using a catalyst of a class represented by formula (II):

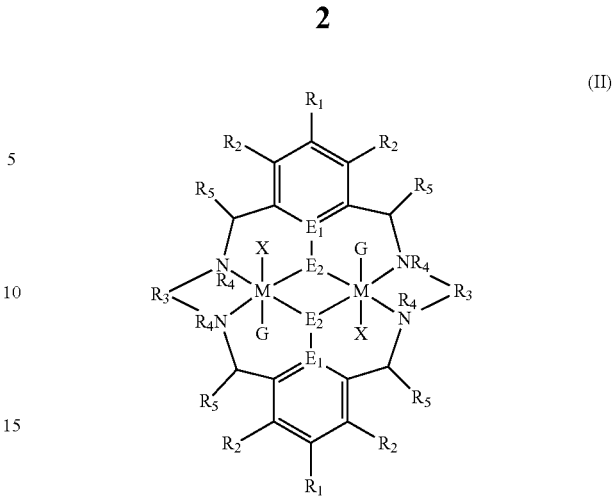

Various compounds according to formulae (I) and (II) above were tested for their ability to catalyse the reaction between different epoxides and carbon dioxide. In both WO2009/130470 and WO2013/034750, M is specified as being selected from Zn(II), Cr(II), Co(II), Mn(II), Mg(II), Fe(II), Ti(II), Cr(III)-X, Co(III)-X, Mn(III)-X, Fe(III)-X, Ca(II), Ge(II), Al(111)-X, Ti(III)-X, V(III)-X, Ge(IV)-(X)$_2$ or Ti(IV)-(X)$_2$.

Among the epoxides employed in the copolymerization reactions of the prior art, cyclohexene oxide (CHO) received special interest, as the product, poly(cyclohexene carbonate) (PCHC) shows a high glass transition temperature and reasonable tensile strength. Ethylene oxide, propylene oxide and butylene oxide have also received interest as they produce polymers (polyalkylene carbonates, such as PPC) with elastomeric properties which are useful in many applications e.g. films.

WO2012/037282 discloses a catalyst of formula:

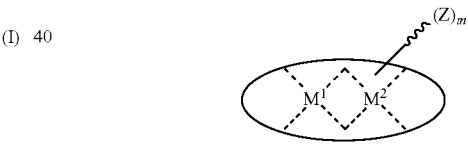

WO2012/037282 indicates that these compounds may be useful for the copolymerisation of an epoxide with $CO_2$. WO2012/037282 states that $M_1$ and $M_2$ can be any metal atom. However, these complexes were not tested to determine which if any possessed the necessary catalytic activity.

The inventors have now surprisingly found that bimetallic catalysts having at least one nickel metal centre, are active as polymerisation catalysts. In particular, the inventors have found that bimetallic catalysts having at least one nickel metal centre, and preferably having two nickel metal centres, are better in terms of activity and/or selectivity than the catalysts previously disclosed in the art. In particular, catalysts of the invention have improved activity in relation to di-substituted meso-epoxides (e.g. cyclohexene oxide) and mono-substituted epoxides (e.g.propylene oxide), and furthermore improved selectivity to mono-substituted epoxides.

SUMMARY OF THE INVENTION

According to a first aspect of the present invention, there is provided a catalyst of formula (I):

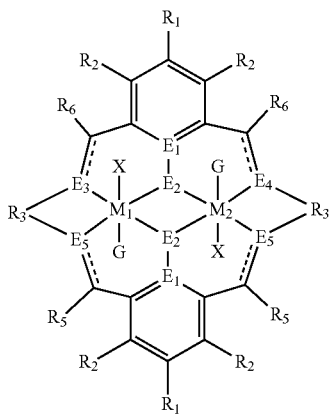

(I)

wherein:
$M_1$ and $M_2$ are independently selected from Zn(II), Cr(II), Co(II), Cu(II), Mn(II), Mg(II), Ni(II), Fe(II), Ti(II), V(II), Cr(III)-X, Co(III)-X, Mn(III)-X, Ni(III)-X, Fe(III)-X, Ca(II), Ge(II), Al(III)-X, Ti(III)-X, V(III)-X, Ge(IV)-(X)$_2$ or Ti(IV)-(X)$_2$;
wherein at least one of $M_1$ or $M_2$ is selected from Ni(II), and Ni(III)-X;
$R_1$ and $R_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;
$R_3$ is independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic; $R_5$ is independently selected from H, or optionally substituted aliphatic, heteroaliphatic, alicyclic, heteroalicyclic, aryl, heteroaryl, alkylheteroaryl or alkylaryl;
E1 is C, E2 is O, S or NH or E1 is N and E2 is O;
E3, E4, E5 and E6 are selected from N, NR4, O and S, wherein when E3, E4, E5 or E6 are N, ====== is ══════ , and wherein when E3, E4, E5 or E6 are NR4, O or S, ====== is ────── ; $R_4$ is independently selected from H, or optionally substituted aliphatic, heteroaliphatic, alicyclic, heteroalicyclic, aryl, heteroaryl, alkylheteroaryl or alkylaryl;
X is independently selected from OC(O)Rx, OSO2Rx, OSORx, OSO(Rx)2, S(O)Rx, ORx, phosphinate, halide, nitrate, hydroxyl, carbonate, amino, nitro, amido or optionally substituted aliphatic, heteroaliphatic, alicyclic, heteroalicyclic, aryl or heteroaryl;
$R_x$ is independently hydrogen, or optionally substituted aliphatic, haloaliphatic, heteroaliphatic, alicyclic, heteroalicyclic, aryl, alkylaryl or heteroaryl; and
G is absent or independently selected from a neutral or anionic donor ligand which is a Lewis base.

In a second aspect of the invention, there is provided a process for the reaction of (i) carbon dioxide with an epoxide, (ii) an anhydride and an epoxide, and/or (iii) a lactide and/or a lactone in the presence of a catalyst according to the first aspect, optionally in the presence of a chain transfer agent.

The third aspect of the invention provides a product of the process of the second aspect of the invention.

In a further aspect, the invention extends to methods of preparation of ligands, complexes and catalysts according to the first aspect and/or as defined herein.

BRIEF DESCRIPTION OF THE DRAWINGS

These and other features, aspects and advantages of the present invention are better understood when the following detailed description of the invention is read with reference to the accompanying drawings, in which.

DEFINITIONS

Figure 1:
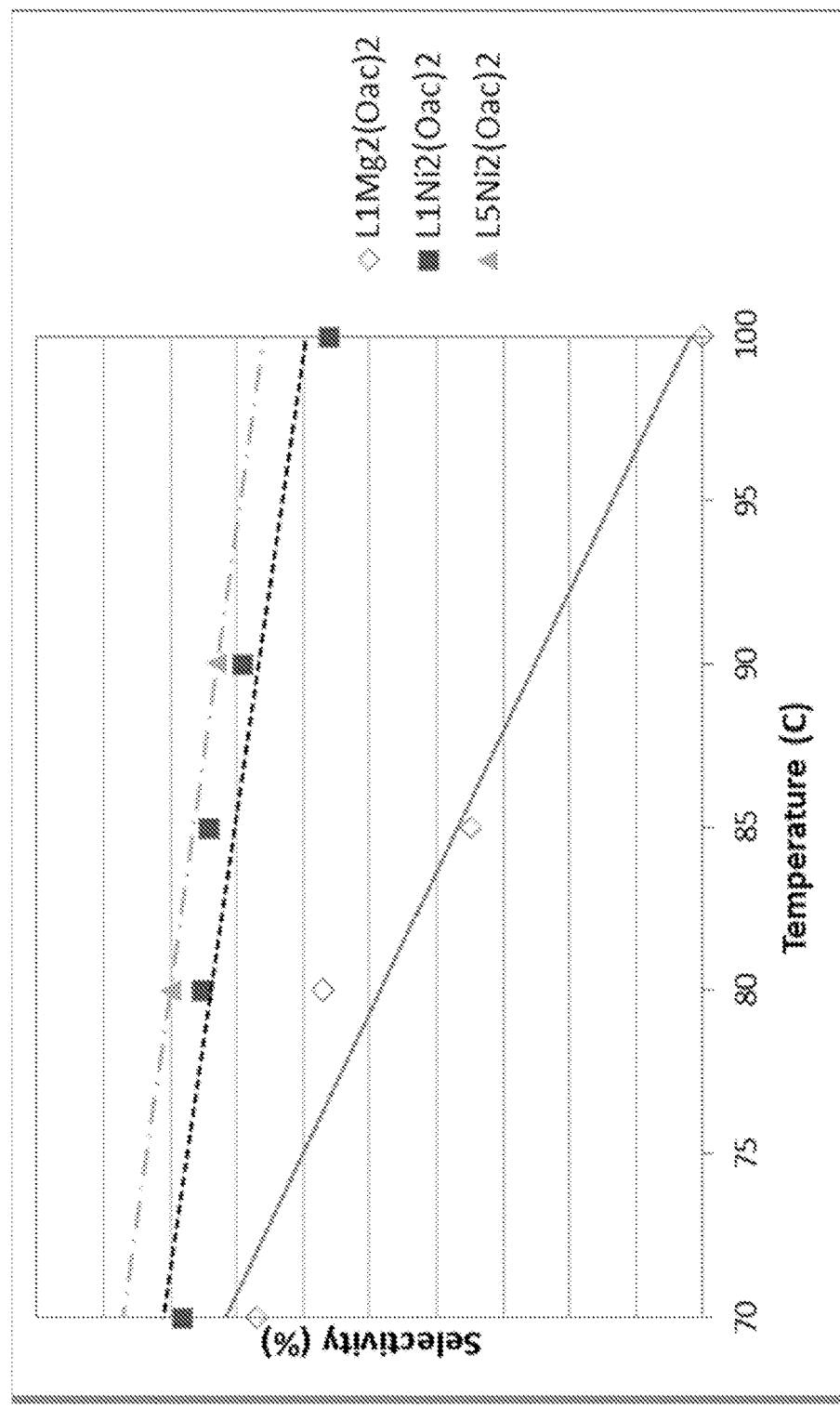
FIG. 1 shows the selectivity of various catalysts.

For the purpose of the present invention, an aliphatic group is a hydrocarbon moiety that may be straight chain or branched and may be completely saturated, or contain one or more units of unsaturation, but which is not aromatic. The term "unsaturated" means a moiety that has one or more double and/or triple bonds. The term "aliphatic" is therefore intended to encompass alkyl, alkenyl or alkynyl groups, and combinations thereof. An aliphatic group is preferably a $C_{1-20}$aliphatic group, that is, an aliphatic group with 1, 2, 3, 4, 5, 6, 7, 8, 9, 10, 11, 12, 13, 14, 15, 16, 17, 18, 19 or 20 carbon atoms. Preferably, an aliphatic group is a $C_{1-15}$aliphatic, more preferably a $C_{1-12}$aliphatic, more preferably a $C_{1-10}$aliphatic, even more preferably a $C_{1-8}$aliphatic, such as a $C_{1-6}$aliphatic group.

An alkyl group is preferably a "$C_{1-20}$ alkyl group", that is an alkyl group that is a straight or branched chain with 1 to 20 carbons. The alkyl group therefore has 1, 2, 3, 4, 5, 6, 7, 8, 9, 10, 11, 12, 13, 14, 15, 16, 17, 18, 19 or 20 carbon atoms. Preferably, an alkyl group is a $C_{1-15}$alkyl, preferably a $C_{1-12}$alkyl, more preferably a $C_{1-10}$alkyl, even more preferably a $C_{1-8}$alkyl, even more preferably a $C_{1-6}$alkyl group. Specifically, examples of "$C_{1-20}$ alkyl group" include methyl group, ethyl group, n-propyl group, iso-propyl group, n-butyl group, iso-butyl group, sec-butyl group, tert-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like.

Alkenyl and alkynyl groups are preferably "$C_{2-20}$alkenyl" and "$C_{2-20}$alkynyl", more preferably "$C_{2-15}$alkenyl" and "$C_{2-15}$alkynyl", even more preferably "$C_{2-12}$alkenyl" and "$C_{2-12}$alkynyl", even more preferably "$C_{2-10}$alkenyl" and "$C_{2-10}$alkynyl", even more preferably "$C_{2-8}$alkenyl" and "$C_{2-8}$alkynyl", most preferably "$C_{2-6}$alkenyl" and "$C_{2-6}$alkynyl" groups, respectively.

A heteroaliphatic group (including heteroalkyl, heteroalkenyl and heteroalkynyl) is an aliphatic group as described above, which additionally contains one or more heteroatoms. Heteroaliphatic groups therefore preferably contain from 2 to 21 atoms, preferably from 2 to 16 atoms, more preferably from 2 to 13 atoms, more preferably from 2 to 11 atoms, more preferably from 2 to 9 atoms, even more preferably from 2 to 7 atoms, wherein at least one atom is a carbon atom. Particularly preferred heteroatoms are selected from O, S, N, P and Si. When heteroaliphatic groups have two or more heteroatoms, the heteroatoms may be the same or different.

An alicyclic group is a saturated or partially unsaturated cyclic aliphatic monocyclic or polycyclic (including fused, bridging and spiro-fused) ring system which has from 3 to 20 carbon atoms, that is an alicyclic group with 3, 4, 5, 6, 7, 8, 9, 10, 11, 12, 13, 14, 15, 16, 17, 18, 19 or 20 carbon atoms. Preferably, an alicyclic group has from 3 to 15, more preferably from 3 to 12, even more preferably from 3 to 10, even more preferably from 3 to 8 carbon atoms, even more preferably from 3 to 6 carbons atoms. The term "alicyclic" encompasses cycloalkyl, cycloalkenyl and cycloalkynyl groups. It will be appreciated that the alicyclic group may comprise an alicyclic ring bearing one or more linking or non-linking alkyl substituents, such as —CH$_2$-cyclohexyl. Specifically, examples of the C$_{3-20}$ cycloalkyl group include cyclopropyl, cyclobutyl, cyclopentyl, cyclohexyl, cycloheptyl, adamantyl and cyclooctyl.

A heteroalicyclic group is an alicyclic group as defined above which has, in addition to carbon atoms, one or more ring heteroatoms, which are preferably selected from O, S, N, P and Si. Heteroalicyclic groups preferably contain from one to four heteroatoms, which may be the same or different. Heteroalicyclic groups preferably contain from 5 to 20 atoms, more preferably from 5 to 14 atoms, even more preferably from 5 to 12 atoms.

An aryl group is a monocyclic or polycyclic ring system having from 5 to 20 carbon atoms. An aryl group is preferably a "C$_{6-12}$ aryl group" and is an aryl group constituted by 6, 7, 8, 9, 10, 11 or 12 carbon atoms and includes condensed ring groups such as monocyclic ring group, or bicyclic ring group and the like. Specifically, examples of "C$_{6-10}$ aryl group" include phenyl group, biphenyl group, indenyl group, naphthyl group or azulenyl group and the like. It should be noted that condensed rings such as indan and tetrahydro naphthalene are also included in the aryl group.

A heteroaryl group is an aryl group having, in addition to carbon atoms, from one to four ring heteroatoms which are preferably selected from O, S, N, P and Si. A heteroaryl group preferably has from 5 to 20, more preferably from 5 to 14 ring atoms. Specifically, examples of a heteroaryl group include pyridine, imidazole, methylimidazole and dimethylaminopyridine.

Examples of alicyclic, heteroalicyclic, aryl and heteroaryl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

The term "halide" or "halogen" are used interchangeably and, as used herein mean a fluorine atom, a chlorine atom, a bromine atom, an iodine atom and the like, preferably a fluorine atom, a bromine atom or a chlorine atom, and more preferably a fluorine atom.

A haloalkyl group is preferably a "C$_{1-20}$ haloalkyl group", more preferably a "C$_{1-18}$ haloalkyl group", more preferably a "C$_{1-12}$ haloalkyl group", more preferably a "C$_{1-10}$ haloalkyl group", even more preferably a "C$_{1-8}$ haloalkyl group", even more preferably a "C$_{1-8}$ haloalkyl group" and is a C$_{1-20}$ alkyl, a C$_{1-15}$ alkyl, a C$_{1-12}$ alkyl, a C$_{1-10}$ alkyl, a C$_{1-8}$ alkyl, or a C$_{1-6}$ alkyl group, respectively, as described above substituted with at least one halogen atom, preferably 1, 2 or 3 halogen atom(s). Specifically, examples of "C$_{1-20}$ haloalkyl group" include fluoromethyl group, difluoromethyl group, trifluoromethyl group, fluoroethyl group, difluroethyl group, trifluoroethyl group, chloromethyl group, bromomethyl group, iodomethyl group and the like.

An alkoxy group is preferably a "C$_{1-20}$ alkoxy group", more preferably a "C$_{1-18}$ alkoxy group", more preferably a "C$_{1-12}$ alkoxy group", more preferably a "C$_{1-10}$ alkoxy group", even more preferably a "C$_{1-8}$ alkoxy group", even more preferably a "C$_{1-8}$ alkoxy group" and is an oxy group that is bonded to the previously defined C$_{1-20}$ alkyl, C$_{1-15}$ alkyl, C$_{1-12}$ alkyl, C$_{1-10}$ alkyl, C$_{1-8}$ alkyl, or C$_{1-6}$ alkyl group respectively. Specifically, examples of "C$_{1-20}$ alkoxy group" include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, n-hexyloxy group, n-heptyloxy group, n-octyloxy group, n-nonyloxy group, n-decyloxy group, n-undecyloxy group, n-dodecyloxy group, n-tridecyloxy group, n-tetradecyloxy group, n-pentadecyloxy group, n-hexadecyloxy group, n-heptadecyloxy group, n-octadecyloxy group, n-nonadecyloxy group, n-eicosyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

An aryloxy group is preferably a "C$_{5-20}$ aryloxy group", more preferably a "C$_{6-12}$ aryloxy group", even more preferably a "C$_{6-10}$ aryloxy group" and is an oxy group that is bonded to the previously defined C$_{5-20}$ aryl, C$_{6-12}$ aryl, or C$_{6-10}$ aryl group respectively.

An alkylthio group is preferably a "C$_{1-20}$ alkylthio group", more preferably a "C$_{1-16}$ alkylthio group", more preferably a "C$_{1-12}$ alkylthio group", more preferably a "C$_{1-10}$ alkylthio group", even more preferably a "C$_{1-8}$ alkylthio group", even more preferably a "C$_{1-6}$ alkylthio group" and is a thio (—S—) group that is bonded to the previously defined C$_{1-20}$ alkyl, C$_{1-15}$ alkyl, C$_{1-12}$ alkyl, C$_{1-10}$ alkyl, C$_{1-8}$ alkyl, or C$_{1-6}$ alkyl group respectively.

An arylthio group is preferably a "C$_{5-20}$ arylthio group", more preferably a "C$_{6-12}$ arylthio group", even more preferably a "C$_{6-10}$ arylthio group" and is an thio (—S—) group that is bonded to the previously defined C$_{5-20}$ aryl, C$_{6-12}$ aryl, or C$_{6-10}$ aryl group respectively.

An alkylaryl group is preferably a "C$_{6-12}$ aryl C$_{1-20}$ alkyl group", more preferably a preferably a "C$_{6-12}$ aryl C$_{1-16}$ alkyl group", even more preferably a "$C_{6-12}$ aryl $C_{1-6}$ alkyl group" and is an aryl group as defined above bonded at any position to an alkyl group as defined above. The point of attachment of the alkylaryl group to a molecule may be via the alkyl portion and thus, preferably, the alkylaryl group is —$CH_2$—Ph or —$CH_2CH_2$—Ph. An alkylaryl group can also be referred to as "aralkyl".

A silyl group is preferably a group —$Si(R_S)_3$, wherein each $R_S$ can be independently an aliphatic, heteroaliphatic, alicyclic, heteroalicyclic, aryl or heteroaryl group as defined above. In certain embodiments, each $R_S$ is independently an unsubstituted aliphatic, alicyclic or aryl. Preferably, each $R_S$ is an alkyl group selected from methyl, ethyl or propyl.

A silyl ether group is preferably a group $OSi(R_6)_3$ wherein each $R_6$ can be independently an aliphatic, heteroaliphatic, alicyclic, heteroalicyclic, aryl or heteroaryl group as defined above. In certain embodiments, each $R_6$ can be independently an unsubstituted aliphatic, alicyclic or aryl. Preferably, each $R_6$ is an optionally substituted phenyl or optionally substituted alkyl group selected from methyl, ethyl, propyl or butyl (such as n-butyl or tert-butyl (tBu)). Exemplary silyl ether groups include $OSi(Me)_3$, $OSi(Et)_3$, $OSi(Ph)_3$, $OSi(Me)_2(tBu)$, $OSi(tBu)_3$ and $OSi(Ph)_2(tBu)$.

A nitrile group (also referred to as a cyano group) is a group CN.

An imine group is a group —CRNR, preferably a group —$CHNR_7$ wherein $R_7$ is an aliphatic, heteroaliphatic, alicyclic, heteroalicyclic, aryl or heteroaryl group as defined above. In certain embodiments, $R_7$ is unsubstituted aliphatic, alicyclic or aryl. Preferably $R_7$ is an alkyl group selected from methyl, ethyl or propyl.

An acetylide group contains a triple bond —C≡C—$R_9$, preferably wherein $R_9$ can be hydrogen, an aliphatic, heteroaliphatic, alicyclic, heteroalicyclic, aryl or heteroaryl group as defined above. For the purposes of the invention when $R_9$ is alkyl, the triple bond can be present at any position along the alkyl chain. In certain embodiments, $R_9$ is unsubstituted aliphatic, alicyclic or aryl. Preferably $R_9$ is methyl, ethyl, propyl or phenyl.

An amino group is preferably —$NH_2$, —$NHR_{10}$ or —$N(R_{10})_2$ wherein $R_{10}$ can be an aliphatic, heteroaliphatic, alicyclic, heteroalicyclic, a silyl group, aryl or heteroaryl group as defined above. It will be appreciated that when the amino group is $N(R_{10})_2$, each $R_{10}$ group can be the same or different. In certain embodiments, each $R_{10}$ is independently an unsubstituted aliphatic, alicyclic, silyl or aryl. Preferably $R_{10}$ is methyl, ethyl, propyl, $SiMe_3$ or phenyl.

An amido group is preferably —$NR_{11}C(O)$— or —$C(O)$—$NR_{11}$— wherein $R_{11}$ can be hydrogen, an aliphatic, heteroaliphatic, alicyclic, heteroalicyclic, aryl or heteroaryl group as defined above. In certain embodiments, $R_{11}$ is unsubstituted aliphatic, alicyclic or aryl. Preferably $R_{11}$ is hydrogen, methyl, ethyl, propyl or phenyl. The amido group may be terminated by hydrogen, an aliphatic, heteroaliphatic, alicyclic, heteroalicyclic, aryl or heteroaryl group.

An ester group is preferably —$OC(O)R_{12}$— or —$C(O)OR_{12}$— wherein $R_{12}$ can be hydrogen, an aliphatic, heteroaliphatic, alicyclic, heteroalicyclic, aryl or heteroaryl group as defined above. In certain embodiments, $R_{12}$ is unsubstituted aliphatic, alicyclic or aryl. Preferably $R_{12}$ is hydrogen, methyl, ethyl, propyl or phenyl. The ester group may be terminated by hydrogen, an aliphatic, heteroaliphatic, alicyclic, heteroalicyclic, aryl or heteroaryl group.

A sulfoxide is preferably —$S(O)R_{13}$ and a sulfonyl group is preferably —$S(O)_2R_{13}$ wherein $R_{13}$ can be hydrogen, an aliphatic, heteroaliphatic, alicyclic, heteroalicyclic, aryl or heteroaryl group as defined above. In certain embodiments, $R_{13}$ is unsubstituted aliphatic, alicyclic or aryl. Preferably $R_{13}$ is hydrogen, methyl, ethyl, propyl or phenyl.

A carboxylate group is preferably —$OC(O)R_{14}$, wherein $R_{14}$ can be hydrogen, an aliphatic, heteroaliphatic, alicyclic, heteroalicyclic, aryl or heteroaryl group as defined above. In certain embodiments, $R_{14}$ is unsubstituted aliphatic, alicyclic or aryl. Preferably $R_{14}$ is hydrogen, methyl, ethyl, propyl, butyl (for example n-butyl, isobutyl or tert-butyl), phenyl, pentafluorophenyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, trifluoromethyl or adamantyl.

An acetamide is preferably $MeC(O)_N(R_{15})_2$ wherein $R_{15}$ can be hydrogen, an aliphatic, heteroaliphatic, alicyclic, heteroalicyclic, aryl or heteroaryl group as defined above. In certain embodiments, $R_{15}$ is unsubstituted aliphatic, alicyclic or aryl. Preferably $R_{15}$ is hydrogen, methyl, ethyl, propyl or phenyl.

A phosphinate group is preferably a group —$OP(O)(R_{16})_2$ or —$P(O)(OR_{16})$ wherein each $R_{16}$ is independently selected from hydrogen, or an aliphatic, heteroaliphatic, alicyclic, heteroalicyclic, aryl or heteroaryl group as defined above. In certain embodiments, $R_{16}$ is aliphatic, alicyclic or aryl, which are optionally substituted by aliphatic, alicyclic, aryl or $C_{1-6}$alkoxy. Preferably $R_{16}$ is optionally substituted aryl or $C_{1-20}$ alkyl, more preferably phenyl optionally substituted by $C_{1-6}$alkoxy (preferably methoxy) or unsubstituted $C_{1-20}$alkyl (such as hexyl, octyl, decyl, dodecyl, tetradecyl, hexadecyl, stearyl).

A sulfinate group is preferably —$OSOR_{17}$ wherein $R_{17}$ can be hydrogen, an aliphatic, heteroaliphatic, haloaliphatic, alicyclic, heteroalicyclic, aryl or heteroaryl group as defined above. In certain embodiments, $R_{17}$ is unsubstituted aliphatic, alicyclic or aryl. Preferably $R_{17}$ is hydrogen, methyl, ethyl, propyl or phenyl.

A carbonate group is preferably $OC(O)OR_{18}$, wherein $R_{18}$ can be hydrogen, an aliphatic, heteroaliphatic, alicyclic, heteroalicyclic, aryl or heteroaryl group as defined above. In certain embodiments, $R_{18}$ is optionally substituted aliphatic, alicyclic or aryl. Preferably $R_{18}$ is hydrogen, methyl, ethyl, propyl, butyl (for example n-butyl, isobutyl or tert-butyl), phenyl, pentafluorophenyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, trifluoromethyl, cyclohexyl, benzyl or adamantyl.

It will be appreciated that where any of the above groups are present in a Lewis base G, one or more additional R groups may be present, as appropriate, to complete the valency. For example, in the context of an amino group, an additional R group may be present to give $RNHR_{10}$, wherein R is hydrogen, an optionally substituted aliphatic, heteroaliphatic, alicyclic, heteroalicyclic, aryl or heteroaryl group as defined above. Preferably, R is hydrogen or aliphatic, alicyclic or aryl.

Any of the aliphatic, heteroaliphatic, alicyclic, heteroalicyclic, aryl, heteroaryl, haloalkyl, alkoxy, aryloxy, alkylthio, arylthio, alkylaryl, silyl, silyl ether, ester, sulfoxide, sulfonyl, carboxylate, carbonate, imine, acetylide, amino, phosphinate, sulfonate or amido groups wherever mentioned in the definitions above, may optionally be substituted by halogen, hydroxy, nitro, carboxylate, carbonate, alkoxy, aryloxy, alkylthio, arylthio, heteroaryloxy, alkylaryl, amino, amido, imine, nitrile, silyl, silyl ether, ester, sulfoxide, sulfonyl, acetylide, phosphinate, sulfonate or optionally substituted aliphatic, heteroaliphatic, alicyclic, heteroalicyclic, aryl or heteroaryl groups (for example, optionally substituted by halogen, hydroxy, nitro, carbonate, alkoxy, aryloxy, alkylthio, arylthio, amino, imine, nitrile, silyl, sulfoxide, sulfonyl, phosphinate, sulfonate or acetylide).

It will be appreciated that although in formula (I), the groups X and G are illustrated as being associated with a single $M_1$ or $M_2$ metal centre, one or more X and G groups may form a bridge between the $M_1$ and $M_2$ metal centres.

For the purposes of the present invention, the epoxide substrate is not limited. The term epoxide therefore relates to any compound comprising an epoxide moiety. Examples of epoxides which may be used in the present invention include, but are not limited to, cyclohexene oxide, styrene oxide, propylene oxide, butylene oxide, substituted cyclohexene oxides (such as limonene oxide, $C_{10}H_{16}O$ or 2-(3,4-epoxycyclohexyl)ethyltrimethoxysilane, $C_{11}H_{22}O$), alkylene oxides (such as ethylene oxide and substituted ethylene oxides), unsubstituted or substituted oxiranes (such as oxirane, epichlorohydrin, 2-(2-methoxyethoxy)methyl oxirane (MEMO), 2-(2-(2-methoxyethoxy)ethoxy)methyl oxirane (ME2MO), 2-(2-(2-(2-methoxyethoxy)ethoxy)ethoxy) methyl oxirane (ME3MO), 1,2-epoxybutane, glycidyl ethers, vinyl-cyclohexene oxide, 3-phenyl-1,2-epoxypropane, 1,2- and 2,3-epoxybutane, isobutylene oxide, cyclopentene oxide, 2,3-epoxy-1,2,3,4-tetrahydronaphthalene indene oxide, and functionalized 3,5-dioxaepoxides. Examples of functionalized 3,5-dioxaepoxides include:

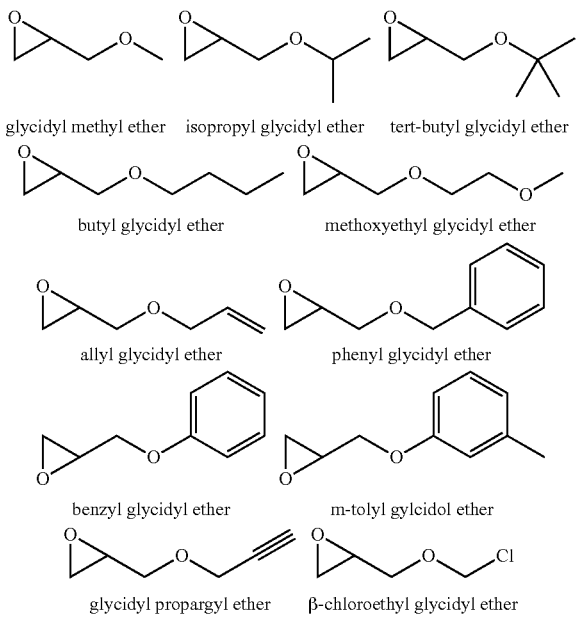

The epoxide moiety may be a glycidyl ether, glycidyl ester or glycidyl carbonate. Examples of glycidyl ethers, glycidyl esters glycidyl carbonates include:

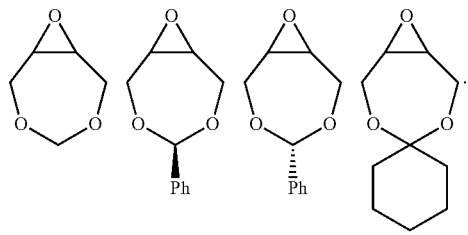

glycidyl methyl ether    isopropyl glycidyl ether    tert-butyl glycidyl ether butyl glycidyl ether    methoxyethyl glycidyl ether allyl glycidyl ether    phenyl glycidyl ether benzyl glycidyl ether    m-tolyl gylcidol ether glycidyl propargyl ether    β-chloroethyl glycidyl ether

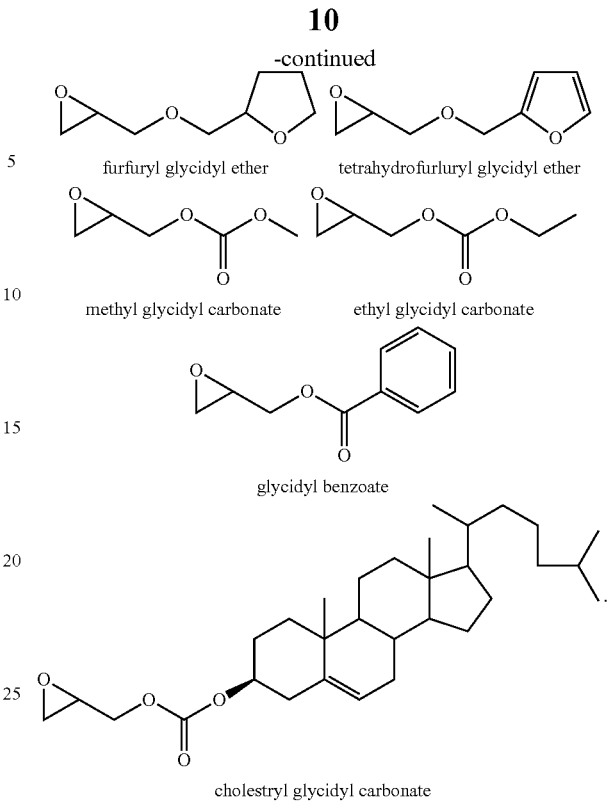

furfuryl glycidyl ether    tetrahydrofurluryl glycidyl ether methyl glycidyl carbonate    ethyl glycidyl carbonate glycidyl benzoate cholestryl glycidyl carbonate The epoxide substrate may contain more than one epoxide moiety, i.e. it may be a bis-epoxide, a tris-epoxide, or a multi-epoxide containing moiety. Examples of compounds including more than one epoxide moiety include bisphenal A diglycidyl ether and 3,4-epoxycyclohexylmethyl 3,4-epoxycyclohexanecarboxylate. It will be understood that reactions carried out in the presence of one or more compounds having more than one epoxide moiety may lead to cross-linking in the resulting polymer.

The skilled person will appreciate that the epoxide can be obtained from "green" or renewable resources. The epoxide may be obtained from a (poly)unsaturated compound, such as those deriving from a fatty acid and/or terpene, obtained using standard oxidation chemistries.

The epoxide moiety may contain —OH moieties, or protected —OH moieties. The —OH moieties may be protected by any suitable protecting group. Suitable protecting groups include methyl or other alkyl groups, benzyl, allyl, tert-butyl, tetrahydropyranyl (THP), methoxymethyl (MOM), acetyl (C(O)alkyl), benzolyl (C(O)Ph), dimethoxytrityl (DMT), methoxyethoxymethyl (MEM), p-methoxybenzyl (PMB), trityl, silyl (such as trimethylsilyl (TMS), t-Butyldimethylsilyl (TBDMS), t-Butyldiphenylsilyl (TBDPS), tri-iso-propylsilyloxymethyl (TOM), and tri-isopropylsilyl (TIPS)), (4-methoxyphenyl)diphenylmethyl (MMT), tetrahydrofuranyl (THF), and tetrahydropyranyl (THP).

The epoxide preferably has a purity of at least 98%, more preferably >99%.

It will be understood that the term "an epoxide" is intended to encompass one or more epoxides. In other words, the term "an epoxide" refers to a single epoxide, or a mixture of two or more different epoxides. For example, the epoxide substrate may be a mixture of ethylene oxide and propylene oxide, a mixture of cyclohexene oxide and propylene oxide, a mixture of ethylene oxide and cyclohexene oxide, or a mixture of ethylene oxide, propylene oxide and cyclohexene oxide.

The skilled person will also understand that substituted and unsubstituted oxetanes can be used in place of, and in addition to, the epoxides of the second aspect of the invention. Suitable oxetanes include unsubstituted or substituted oxetanes (preferably substituted at the 3-position by halogen, alkyl (unsubstituted or substituted by —OH or halogen), amino, hydroxyl, aryl (e.g. phenyl), alkylaryl (e.g. benzyl)). Exemplary oxetanes include oxetane, 3-ethyl-3-oxetanemethanol, oxetane-3-methanol, 3-methyl-3-oxetanemethanol, 3-methyloxetane, 3-ethyloxetane, etc.

The term anhydride relates to any compound comprising an anhydride moiety in a ring system (i.e. a cyclic anhydride). Preferably, the anhydrides which are useful in the present invention have the following formula:

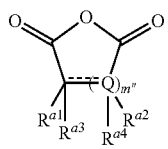

Wherein m" is 1, 2, 3, 4, 5, or 6 (preferably 1 or 2), each $R^{a1}$, $R^{a2}$, $R^{a3}$ and $R^{a4}$ is independently selected from hydrogen, halogen, hydroxyl, nitro, alkoxy, aryloxy, heteroaryloxy, amino, alkylamino, imine, nitrile, acetylide, carboxylate or optionally substituted aliphatic, heteroaliphatic, alicyclic, heteroalicyclic, aryl, heteroaryl, alkylaryl or alkylheteroaryl; or two or more of $R^{a1}$, $R^{a2}$, $R^{a3}$ and $R^{a4}$ can be taken together to form a saturated, partially saturated or unsaturated 3 to 12 membered, optionally substituted ring system, optionally containing one or more heteroatoms, or can be taken together to form a double bond. Each Q is independently C, O, N or S, preferably C, wherein $R^{a3}$ and $R^{a4}$ are either present, or absent, and ===== can either be ===== or ———, according to the valency of Q. It will be appreciated that when Q is C, and ===== is =====, $R^{a3}$ and $R^{a4}$ (or two $R^{a4}$ on adjacent carbon atoms) are absent. The skilled person will appreciate that the anhydrides may be obtained from "green" or renewable resources. Preferable anhydrides are set out below.

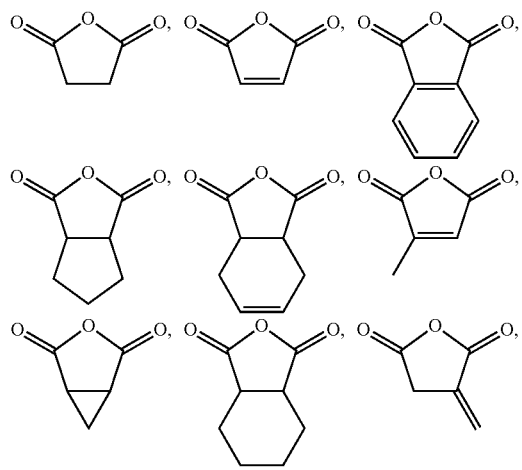

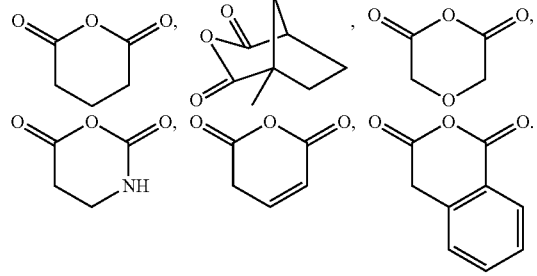

The term lactone relates to any cyclic compound comprising a —C(O)O— moiety in the ring. Preferably, the lactones which are useful in the present invention have the following formula:

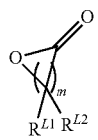

Wherein m is 1 to 20 (e.g. 1, 2, 3, 4, 5, 6, 7, 8, 9, 10, 11, 12, 13, 14, 15, 16, 17, 18, 19 or 20), preferably 2, 4, or 5; and $R^{L1}$ and $R^{L2}$ are independently selected from hydrogen, halogen, hydroxyl, nitro, alkoxy, aryloxy, heteroaryloxy, amino, alkylamino, imine, nitrile, acetylide, carboxylate or optionally substituted aliphatic, heteroaliphatic, alicyclic, heteroalicyclic, aryl, heteroaryl, alkylaryl or alkylheteroaryl. Two or more of $R^{L1}$ and $R^{L2}$ can be taken together to form a saturated, partially saturated or unsaturated 3 to 12 membered, optionally substituted ring system, optionally containing one or more heteroatoms. When m is 2 or more, the $R^{L1}$ and $R^{L2}$ on each carbon atom may be the same or different. Preferably $R^{L1}$ and $R^{L2}$ are selected from hydrogen or alkyl. Preferably, the lactone has the following structure:

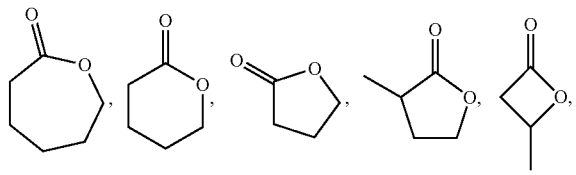

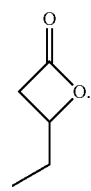

The term lactide is a cyclic compound containing two ester groups. Preferably, the lactides which are useful in the present invention have the following formula:

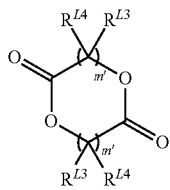

Wherein m' is 1, 2, 3, 4, 5, 6, 7, 8, 9 or 10, (preferably 1 or 2, more preferably, 1) and $R^{L3}$ and $R^{L4}$ are independently selected from hydrogen, halogen, hydroxyl, nitro, alkoxy, aryloxy, heteroaryloxy, amino, alkylamino, imine, nitrile, acetylide, carboxylate or optionally substituted aliphatic, heteroaliphatic, alicyclic, heteroalicyclic, aryl, heteroaryl, alkylaryl or alkylheteroaryl. Two or more of $R^{L3}$ and $R^{L4}$ can be taken together to form a saturated, partially saturated or unsaturated 3 to 12 membered, optionally substituted ring system, optionally containing one or more heteroatoms, When m' is 2 or more, the $R^{L3}$ and $R^{L4}$ on each carbon atom may be the same or different or one or more $R^{L3}$ and $R^{L4}$ on adjacent carbon atoms can be absent, thereby forming a double or triple bond. It will be appreciated that while the compound has two moieties represented by $(-CR^{L3}R^{L4})_{m'}$, both moieties will be identical. Preferably, m' is 1, $R^{L4}$ is H, and $R^{L3}$ is H, hydroxyl or a $C_{1-6}$alkyl, preferably methyl. The stereochemistry of the moiety represented by $(-CR^{L3}R^{L4})_{m'}$ can either be the same (for example RR-lactide or SS-lactide), or different (for example, meso-lactide). The lactide may be a racemic mixture, or may be an optically pure isomer. Preferably, the lactide has the following formula:

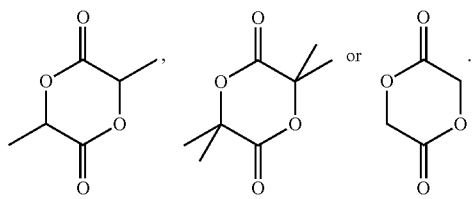

The term "lactone and/or lactide" used herein encompasses a lactone, a lactide and a combination of a lactone and a lactide. Preferably, the term "lactone and/or lactide" means a lactone or a lactide.

Preferred optional substituents of the groups $R^{a1}$, at $R^{a2}$, $R^{a3}$, $R^{a4}$, $R^{L1}$, $R^{L2}$, $R^{L3}$ and $R^{L4}$ include halogen, nitro, hydroxyl, unsubstituted aliphatic, unsubstituted heteroaliphatic unsubstituted aryl, unsubstituted heteroaryl, alkoxy, aryloxy, heteroaryloxy, amino, alkylamino, imine, nitrile, acetylide, and carboxylate.

DETAILED DESCRIPTION

In the first aspect of the invention, there is provided a catalyst of formula (I):

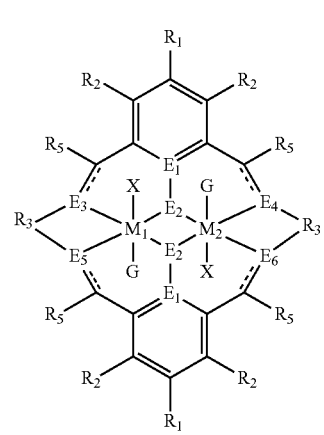

wherein:
$M_1$ and $M_2$ are independently selected from Zn(II), Cr(II), Co(II), Cu(II), Mn(II), Mg(II), Ni(II), Fe(II), Ti(II), V(II), Cr(III)-X, Co(III)-X, Mn(III)-X, Ni(III)-X, Fe(III)-X, Ca(II), Ge(II), Al(III)-X, Ti(III)-X, V(III)-X, Ge(IV)-(X)$_2$ or Ti(IV)-(X)$_2$;
wherein at least one of $M_1$ or $M_2$ is selected from Ni(II) and Ni(III)-X; $R_1$ and $R_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;
$R_3$ is independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic;
$R_5$ is independently selected from H, or optionally substituted aliphatic, heteroaliphatic, alicyclic, heteroalicyclic, aryl, heteroaryl, alkylheteroaryl or alkylaryl;
E1 is C, E2 is O, S or NH or E1 is N and E2 is O;
E3, E4, E5 and E6 are selected from N, NR4, O and S, wherein when E3, E4, E5 or E6 are N, ===== is ═══, and wherein when E3, E4, E5 or E6 are NR4, O or S, ===== is ───; $R_4$ is independently selected from H, or optionally substituted aliphatic, heteroaliphatic, alicyclic, heteroalicyclic, aryl, heteroaryl, alkylheteroaryl or alkylaryl;
X is independently selected from OC(O)Rx, OSO2Rx, OSORx, OSO(Rx)2, S(O)Rx, ORx, phosphinate, halide, nitrate, hydroxyl, carbonate, amino, amido or optionally substituted aliphatic, heteroaliphatic, alicyclic, heteroalicyclic, aryl or heteroaryl;
$R_x$ is independently hydrogen, or optionally substituted aliphatic, haloaliphatic, heteroaliphatic, alicyclic, heteroalicyclic, aryl, alkylaryl or heteroaryl; and
G is absent or independently selected from a neutral or anionic donor ligand which is a Lewis base.
Each of the occurrences of the groups $R_1$ and $R_2$ may be the same or different. Preferably $R_1$ and $R_2$ are independently selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio. Preferably $R_2$ is the same. Preferably, each occurrence of $R_2$ is the same, and is hydrogen.

Even more preferably, $R_2$ is hydrogen and $R_1$ is independently selected from hydrogen, halide, amino, nitro, sulfoxide, sulfonyl, sulfinate, silyl, silyl ether and optionally substituted alkyl, alkenyl, aryl, heteroaryl, alkoxy, aryloxy, alkylthio, arylthio, such as hydrogen, $C_{1-6}$alkyl (e.g. haloalkyl), alkoxy, aryl, halide, nitro, sulfonyl, silyl and alkylthio, for example, $^{t}$Bu, iPr, Me, OMe, H, nitro, $SO_2$Me, $SiEt_3$, halogen or phenyl.

Each occurrence of $R_1$ can be the same or different, and $R_1$ and $R_2$ can be the same or different. Preferably each occurrence of $R_1$ is the same. Preferably each occurrence of $R_2$ is the same. Preferably, each occurrence of $R^1$ is the same, and each occurrence of $R_2$ is the same, and $R_1$ is different to $R_2$.

Preferably both occurrences of $R_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio. More preferably both occurrences of $R_1$ are the same, and are selected from halide, sulfoxide, silyl, and an optionally substituted alkyl, heteroaryl or alkoxy. Still more preferably both occurrences of $R_1$ are the same, and are selected from tbutyl, methoxy, trialkylsilyl such as triethylsilyl, bromide, methanesulfonyl, or piperidinyl. More preferably still both occurrences of $R_1$ are the same, and are selected from t-butyl or trialkylsilyl. Most preferably, both occurrences of $R_1$ are the same, and are tbutyl.

It will be appreciated that the group $R_3$ can be a disubstituted alkyl, alkenyl, alkynyl, heteroalkyl, heteroalkenyl or heteroalkynyl group which may optionally be interrupted by an aryl, heteroaryl, alicyclic or heteroalicyclic group, or may be a disubstituted aryl or cycloalkyl group which acts as a bridging group between two nitrogen centres in the catalyst of formula (I). Thus, where $R_3$ is an alkylene group, such as dimethylpropylenyl, the $R_3$ group has the structure —$CH_2$—$C(CH_3)_2$—$CH_2$—. The definitions of the alkyl, aryl, cycloalkyl etc groups set out above therefore also relate respectively to the divalent alkylene, arylene, cycloalkylene etc groups set out for R3, and may be optionally substituted. Exemplary options for R3 include ethylenyl, 2,2-fluoropropylenyl, 2,2-dimethylpropylenyl, propylenyl, butylenyl, phenylenyl, cyclohexylenyl or biphenylenyl. When R3 is cyclohexylenyl, it can be the racemic, RR- or SS-forms.

$R_3$ can be independently selected from substituted or unsubstituted alkylene and substituted or unsubstituted arylene, preferably substituted or unsubstituted propylenyl, such as propylenyl and 2,2-dimethylpropylenyl, and substituted or unsubstituted phenylenyl or biphenylenyl. Preferably both occurrences of $R_3$ are the same. Even more preferably $R_3$ is a substituted propylenyl, such as 2,2-di (alkyl)propylenyl, especially 2,2-di(methyl)propylenyl.

$R_3$ can be independently selected from substituted or unsubstituted alkylene, alkenylene, alkynylene, heteroalkylene, heteroalkenylene or heteroalkynylene, arylene or cycloalkylene. Preferably, $R_3$ is selected from substituted or unsubstituted alkylene, cycloalkylene, alkenylene, heteroalkylene and arylene. More preferably, $R_3$ is selected from 2,2-dimethylpropylenyl, —$CH_2$ $CH_2$ $CH_2$—, —$CH_2CH(CH_3)CH_2$—, —$CH_2C(CH_2C_6H_5)_2CH_2$—, phenylene, —$CH_2$ $CH_2$—, —$CH_2$ $CH_2$ $CH_2$ $CH_2$—, —$CH_2$ $CH_2N$ ($CH_3$) $CH_2$ $CH_2$—, 1,4-cyclohexandiyl or —$CH_2CH_2CH$ ($C_2H_5$)—. Still more preferably $R_3$ is selected from 2,2-dimethylpropylenyl, —$CH_2$ $CH_2$ $CH_2$—, —$CH_2CH(CH_3)CH_2$—, 13 $CH_2C(CH_2C_6H_5)_2CH_2$—, —$CH_2CH_2CH$ ($C_2H_5$)—, —$CH_2$ $CH_2$ $CH_2$ $CH_2$—. More preferably still, $R_3$ is selected from 2,2-dimethylpropylenyl, —$CH_2C(CH_2C_6H_5)_2CH_2$—, $CH_2CH(CH_3)CH_2$ and —$CH_2C(C_2H_5)_2CH_2$—.

Most preferably R3 is a substituted propylenyl, such as 2,2-di(alkyl)propylenyl, more preferably 2,2-dimethylpropylenyl.

Preferably each $R_4$ is independently selected from hydrogen, and an optionally substituted alkyl, alkenyl, alkynyl, aryl, heteroalkyl, heteroalkenyl, heteroalkynyl or heteroaryl. Preferably $R_4$ is hydrogen. Preferably each $R_4$ is the same. Preferably, each $R_4$ is the same, and is selected from hydrogen, and an optionally substituted alkyl, alkenyl, alkynyl, aryl, heteroalkyl, heteroalkenyl, heteroalkynyl or heteroaryl. Exemplary options for $R_4$ include H, Me, Et, Bn, iPr, tBu or Ph. A further exemplary option is —$CH_2$-(pyridine). Even more preferably, each $R_4$ is hydrogen.

Preferably each $R_5$ is independently selected from hydrogen, and optionally substituted aliphatic or aryl. More preferably, each $R_5$ is independently selected from hydrogen, and optionally substituted alkyl or aryl. Even more preferably, each $R_5$ is the same, and is selected from hydrogen, and optionally substituted alkyl or aryl. Exemplary $R_5$ groups include hydrogen, methyl, ethyl, phenyl and trifluoromethyl, preferably hydrogen, methyl or trifluoromethyl. Even more preferably, each $R_5$ is hydrogen.

Preferably both occurrences of $E_1$ are C and both occurrences of $E_2$ are the same, and selected from O, S or NH. Even more preferably, both occurrences of $E_1$ are C and both occurrences of $E_2$ are O.

Preferably, each occurrence of E3, E4, E5 and E6 are NR4. Even more preferably, E3, E4, E5 and E6 are the same and are NH. In other words, the catalyst of the first aspect preferably has the following preferred structure:

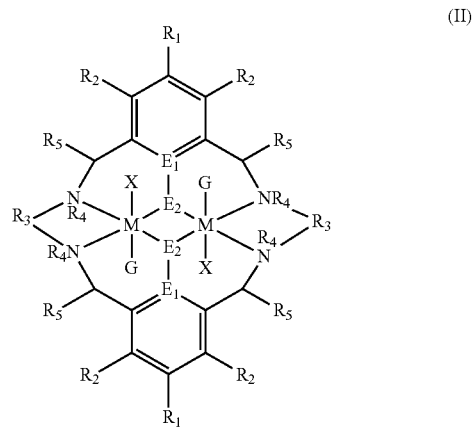

(II)

Each X is independently selected from OC(O)Rx, $OSO_2R^X$, $OS(O)R^X$, $OSO(R^X)_2$, $S(O)R^X$, $OR^X$, phosphinate, halide, nitro, hydroxyl, carbonate, amino, nitrate, amido and optionally substituted, aliphatic, heteroaliphatic (for example silyl), alicyclic, heteroalicyclic, aryl or heteroaryl. Preferably each X is independently $OC(O)R^X$, $OSO_2R^X$, $OS(O)R^X$, $OSO(R^X)_2$, $S(O)R^X$, $OR^X$, halide, nitrate, hydroxyl, carbonate, amino, nitro, amido, alkyl (e.g. branched alkyl), heteroalkyl, (for example silyl), aryl or heteroaryl. Even more preferably, each X is independently $OC(O)R^X$, $OR^X$, halide, carbonate, amino, nitro, alkyl, aryl, heteroaryl, phosphinate or $OSO_2Rx$. Preferred optional substituents for when X is aliphatic, heteroaliphatic, alicyclic, heteroalicyclic, aryl or heteroaryl include halogen, hydroxyl, nitro, cyano, amino, or substituted or unsubstituted aliphatic, heteroaliphatic, alicyclic, heteroalicyclic, aryl or heteroaryl. Each X may be the same or different and preferably each X is the same. It will also be appreciated that X may form a bridge between the two metal centres.

$R^X$ is independently hydrogen, or optionally substituted aliphatic, haloaliphatic, heteroaliphatic, alicyclic, heteroalicyclic, aryl, alkylaryl, or heteroaryl. Preferably, $R^X$ is alkyl, alkenyl, alkynyl, heteroalkyl, aryl, heteroaryl, cycloalkyl, or alkylaryl. Preferred optional substitutents for $R^X$ include halogen, hydroxyl, cyano, nitro, amino, alkoxy, alkylthio, or substituted or unsubstituted aliphatic, heteroaliphatic, alicyclic, heteroalicyclic, aryl or heteroaryl (e.g. optionally substituted alkyl, aryl, or heteroaryl).

Exemplary options for X include OAc, $OC(O)CF_3$, halogen, $OSO(CH_3)_2$, Et, Me, OMe, OiPr, OtBu, Cl, Br, I, F, $N(iPr)_2$ or $N(SiMe_3)_2$, OPh, OBn, salicylate, dioctyl phosphinate, etc.

Preferably each X is the same, and is selected from $OC(O)R^X$, $OR^X$, halide, carbonate, amino, nitro, alkyl, aryl, heteroaryl, phosphinate or $OSO_2R^X$, $R^X$ is alkyl, alkenyl, alkynyl, heteroalkyl, aryl, heteroaryl or alkylaryl. More preferably each X is the same and is $OC(O)R^X$, $OR^X$, halide, alkyl, aryl, heteroaryl, phosphinate or $OSO_2R^X$. Still more preferably each X is the same and is $OC(O)R^X$ More preferably still each X is the same and is selected from OAc, $C_2CCF_3$, or $C_2C(CH_2)_3Cy$. Most preferably each X is the same and is OAc.

Preferably each $R^X$ is the same and is selected from an optionally substituted alkyl, alkenyl, alkynyl, heteroalkyl, aryl, heteroaryl, cycloalkyl or alkylaryl. More preferably each $R^X$ is the same and is an optionally substituted alkyl, alkenyl, heteroalkyl, aryl, heteroaryl, cycloalkyl or alkylaryl. Still more preferably each $R^X$ is the same and is an optionally substituted alkyl, alkenyl, heteroalkyl; or cycloalkyl. More preferably still $R^X$ is an optionally substituted alkyl, heteroalkyl or cycloalkyl. Most preferably $R^X$ is an optionally substituted alkyl.

As detailed above, $M_1$ and $M_2$ are independently selected from any of: Zn(II), Cr(III)-X, Cr(II), Co(III)-X, Co(II), Cu(II), Mn(III)-X, Mn(II), Mg(II), Ni(II), Ni(III)-X, Fe(II), Fe(III)-X, Ca(II), Ge(II), Ti(II), Al(III)-X, Ti(III)-X, V(II), V(III)-X, Ge(IV)-(X)2 or Ti(IV)-(X)2, wherein at least one of $M_1$ and $M_2$ is selected from Ni(II) and Ni(III)-X, still more preferably however at least one of $M_1$ and $M_2$ is Ni(II).

Preferably, $M_1$ and $M_2$ are independently selected from Zn(II), Cr(III)-X, Co(II), Cu(II), Mn(II), Mg(II), Ni(II), Ni(III)-X, Fe(II), Fe(III) and V(II), even more preferably, $M_1$ and $M_2$ are independently selected from Zn(II), Cr(III)-X, Co(II), Mn(II), Mg(II), Ni(II), Ni(III)-X, Fe(II), and Fe(III)-X, and even more preferably, $M_1$ and $M_2$ are independently selected from Zn(II), Mg(II), Ni(II) and Ni(III)-X, wherein at least one of $M_1$ and $M_2$ is selected from Ni(II) and Ni(III)-X, still more preferably at least one of $M_1$ and $M_2$ is Ni(II).

Most preferably, both $M_1$ and $M_2$ are selected from Ni(II) and Ni(III)-X, still most preferably both $M_1$ and $M_2$ are Ni(II).

It will be appreciated that when one of $M_1$ or $M_2$ is Cr(III), Co(III), Mn(III), Ni(III), Fe(III), Al(III), Ti(III) or V(III) the catalyst of formula (I) will contain an additional X group co-ordinated to the metal centre, wherein X is as defined above. It will also be appreciated that when one of $M_1$ or $M_2$ is Ge(IV) or Ti(IV), the catalyst of formula (III) will contain two additional X group co-ordinated to the metal centre, wherein X is as defined above. In certain embodiments, when one of $M_1$ or $M_2$ is Ge(IV)-$(X)_2$ or Ti(IV)-$(X)_2$, both G may be absent.

When G is not absent, it is a group which is capable of donating a lone pair of electrons (i.e. a Lewis base). In certain embodiments, G is a nitrogen-containing Lewis base. Each G may be neutral or negatively charged. If G is negatively charged, then one or more positive counterions will be required to balance out the charge of the complex. Suitable positive counterions include group 1 metal ions ($Na^+$, $K^+$, etc), group 2 metal ions ($Mg^{2+}$, $Ca^{2+}$, etc), imidazolium ions, a positively charged optionally substituted heteroaryl, heteroaliphatic or heteroalicyclic group, ammonium ions (i.e. $N(R^{12})_4^+$), iminium ions (i.e. $(R^{12})_2C=N(R^{12})_2^+$, such as bis(triphenylphosphine)iminium ions) or phosphonium ions ($P(R^{12})_4^+$), wherein each $R^{12}$ is independently selected from hydrogen or optionally substituted aliphatic, heteroaliphatic, alicyclic, heteroalicyclic, aryl or heteroaryl. Exemplary counterions include [H-B]$^+$wherein B is selected from triethylamine, 1,8-diazabicyclo[5.4.0]undec-7-ene and 7-methyl-1,5,7-triazabicyclo [4.4.0]dec-5-ene.

G is preferably independently selected from an optionally substituted heteroaliphatic group, an optionally substituted heteroalicyclic group, an optionally substituted heteroaryl group, a halide, hydroxide, hydride, a carboxylate and water. More preferably, G is independently selected from water, an alcohol (e.g. methanol), a substituted or unsubstituted heteroaryl (imidazole, methyl imidazole (for example, N-methyl imidazole), pyridine, 4-dimethylaminopyridine, pyrrole, pyrazole, etc), an ether (dimethyl ether, diethylether, cyclic ethers, etc), a thioether, carbene, a phosphine, a phosphine oxide, a substituted or unsubstituted heteroalicyclic (morpholine, piperidine, tetrahydrofuran, tetrahydrothiophene, etc), an amine, an alkyl amine trimethylamine, triethylamine, etc), acetonitrile, an ester (ethyl acetate, etc), an acetamide (dimethylacetamide, etc), a sulfoxide (dimethylsulfoxide, etc), a carboxylate, a hydroxide, hydride, a halide, a nitrate, a sulfonate, etc. In some embodiments, one or both instances of G is independently selected from optionally substituted heteroaryl, optionally substituted heteroaliphatic, optionally substituted heteroalicyclic, halide, hydroxide, hydride, an ether, a thioether, carbene, a phosphine, a phosphine oxide, an amine, an alkyl amine, acetonitrile, an ester, an acetamide, a sulfoxide, a carboxylate, a nitrate or a sulfonate. In certain embodiments, G may be a halide; hydroxide; hydride; water; a heteroaryl, heteroalicyclic or carboxylate group which are optionally substituted by alkyl, alkenyl, alkynyl, alkoxy, halogen, hydroxyl, nitro or nitrile. In preferred embodiments, G is independently selected from halide; water; a heteroaryl optionally substituted by alkyl (e.g. methyl, ethyl etc), alkenyl, alkynyl, alkoxy (preferably methoxy), halogen, hydroxyl, nitro or nitrile. In some embodiments, one or both instances of G is negatively charged (for example, halide). In further embodiments, one or both instances of G is an optionally substituted heteroaryl. Exemplary G groups include chloride, bromide, pyridine, methylimidazole (for example N-methyl imidazole) and dimethylaminopyridine (for example, 4-methylaminopyridine).

It will be appreciated that when a G group is present, the G group may be associated with a single M metal centre as shown in formula (I), or the G group may be associated with both metal centres and form a bridge between the two metal centres, as shown below in formula (Ia):

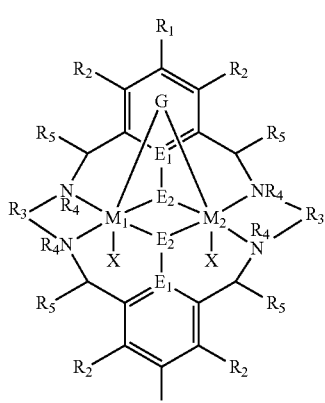

(Ia)

Wherein $R_1$, $R_2$, $R_3$, $R_4$, $R_5$, $M_1$, $M_2$, G, X, $E_1$ and $E_2$, are as defined for formula (I) and formula (II).

It will also be appreciated that X may form a bridge between the two metal centres.

The skilled person will understand that, in the solid state, the catalysts of the first aspect may be associated with solvent molecules such as water, or alcohol (e.g. methanol or ethanol). It will be appreciated that the solvent molecules may be present in a ratio of less than 1:1 relative to the molecules of catalyst of the first aspect (i.e. 0.2:1, 0.25:1, 0.5:1), in a ratio of 1:1, relative to the molecules of catalyst of the first aspect, or in a ratio of greater than 1:1, relative to the molecules of catalyst of the first aspect.

The skilled person will understand that, in the solid state, the catalysts of the first aspect may form aggregates. For example, the catalyst of the first aspect may be a dimer, a trimer, a tetramer, a pentamer, or higher aggregate.

It will be appreciated that the preferred features described above for the catalyst of the first aspect may be present in combination mutatis mutandis.

For example, in preferred embodiments of the first aspect, each occurrence of R2 and R5 are H, E1 is C and E2 is O, S or NH (preferably $E_2$ is O) and, E3-E6 are NR4.

Preferably, each occurrence of $R_2$ and $R_5$ are H, $R_3$ is an optionally substituted or unsubstituted alkylene and substituted or unsubstituted arylene wherein alkylene, may optionally be interrupted by aryl, heteroaryl, alicyclic or heteroalicyclic, $E_1$ is C and $E_2$ is O, S or NH (preferably $E_2$ is O), each occurrence of $E_3$ to $E_6$ is $NR_4$, $R_4$ is hydrogen or alkyl (preferably hydrogen), each X is independently $OC(O)R^X$, $OR^X$, halide, carbonate, amino, nitro, alkyl, aryl, heteroaryl, phosphinate or $OSO_2R^X$, $R^X$ is alkyl, alkenyl, alkynyl, heteroalkyl, aryl, heteroaryl or alkylaryl, each $R_1$ is independently hydrogen, alkyl, alkenyl, aryl, heteroaryl, alkoxy, alkylthio, halide, amino, nitro, sulfoxide, sulfonyl, sulfinate, silyl or silyl ether, each G (where present) is independently selected from halide; water; a heteroaryl optionally substituted by alkyl (e.g. methyl, ethyl etc), alkenyl, alkynyl, alkoxy (preferably methoxy), halogen, hydroxyl, nitro or nitrile, at least one of $M_1$ and $M_2$ is Ni(II) or Ni(III)-X, and the remaining $M_1$ or $M_2$ is selected from Mg(II), Zn(II), Cr(III)-X, Co(II), Co(III)-X, Mn(II), Ni(II), Ni(III)-X, Fe(II), and Fe(III)-X.

Even more preferably, each occurrence of $R_2$ and $R_5$ are H, $R_3$ is an optionally substituted or unsubstituted alkylene and substituted or unsubstituted arylene, $E_1$ is C and $E_2$ is O, S or NH (preferably $E_2$ is O), each occurrence of $E_3$ to $E_6$ is N $R_4$, $R_4$ is hydrogen or alkyl (preferably hydrogen), each X is the same, and is $OC(O)R^X$, $OR^X$, halide, carbonate, amino, nitro, alkyl, aryl, heteroaryl, phosphinate or $OSO_2R^X$, $R^X$ is alkyl, alkenyl, alkynyl, heteroalkyl, aryl, heteroaryl or alkylaryl, each $R_1$ is the same and is hydrogen, alkyl, alkenyl, aryl, heteroaryl, alkoxy, alkylthio, halide, amino, nitro, sulfoxide, sulfonyl, sulfinate, silyl or silyl ether and an optionally substituted alkyl, alkenyl, aryl, heteroaryl, alkoxy or alkylthio, each G (where present) is independently selected from halide; water; a heteroaryl optionally substituted by alkyl (e.g. methyl, ethyl etc), alkenyl, alkynyl, alkoxy (preferably methoxy), halogen, hydroxyl, nitro or nitrile, at least one of $M_1$ and $M_2$ is Ni(II) or Ni(III)-X, and the remaining $M_1$ or $M_2$ is selected from Mg(II), Zn(II), Cr(II), Cr(III)-X, Co(II), Co(III)-X, Mn(II), Ni(II), Ni(III)-X, Fe(II), and Fe(III)-X, preferably both $M_1$ and $M_2$ are selected from Ni(II) and Ni(III)-X.

In a preferred embodiment, the catalyst of formula (I) has the formula (Ib):

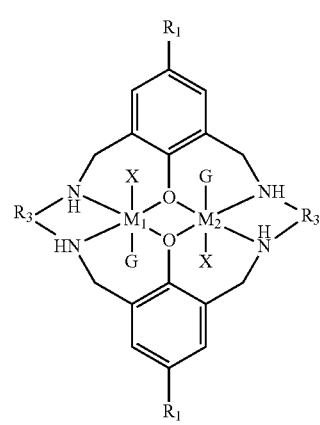

(Ib)

Wherein:

Both occurrences of $R_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio;

$R_3$ is selected from substituted or unsubstituted alkylene, heteroalkylene arylene or heteroarylene wherein alkylene and heteroalkylene may optionally be interrupted by aryl, heteroaryl, alicyclic or heteroalicyclic;

Each X is the same, and is selected from $OC(O)R^X$, $OR^X$, halide, carbonate, amino, nitro, alkyl, aryl, heteroaryl, phosphinate or $OSO_2R^X$, $R^X$ is alkyl, alkenyl, alkynyl, heteroalkyl, aryl, heteroaryl or alkylaryl;

$R^X$ is alkyl, alkenyl, alkynyl, heteroalkyl, aryl, heteroaryl or alkylaryl;

Each G (where present) is independently selected from halide; water; a heteroaryl optionally substituted by alkyl, alkenyl, alkynyl, alkoxy, halogen, hydroxyl, nitro or nitrile; and at least one of $M_1$ and $M_2$ is Ni(II) or Ni(III)-X, and the remaining $M_1$ or $M_2$ is selected from Mg(II), Zn(II), Cr(III)-X, Co(II), Co(III)-X, Mn(II), Ni(II), Ni(III)-X, Fe(II), and Fe(III)-X.

Preferably $R_1$ is hydrogen, halide, silyl, silyl ether, sulfonyl, and optionally substituted alkyl, aryl or alkoxy.

Preferably, $R_3$ is selected from propylenyl, 2,2-dimethylpropylenyl, and substituted or unsubstituted phenylenyl or biphenylenyl. Even more preferably $R_3$ is a substituted propylenyl, such as 2,2-di(alkyl)propylenyl.

Preferably, both $M_1$ and $M_2$ are selected from Ni(II) and Ni(III)-X. Even more preferably, both $M_1$ and $M_2$ are Ni(II).

Preferably, X is $OC(O)R^X$, $OR^X$, halide, alkyl, aryl, heteroaryl, phosphinate or $OSO_2R^X$. Preferably, $R^X$ is alkyl, alkenyl, alkynyl, heteroalkyl, aryl, heteroaryl or alkylaryl. Even more preferably, X is $OC(O)R^X$, and $R^X$ is alkyl, alkenyl, heteroalkyl, aryl, heteroaryl or alkylaryl, preferably $R^X$ is alkyl (e.g. methyl, ethyl, propyl, t-butyl or trifluoromethyl).

G may be absent or present, and preferably G is absent.

In a more preferred embodiment, the catalyst of formula (I) has the formula (Ic):

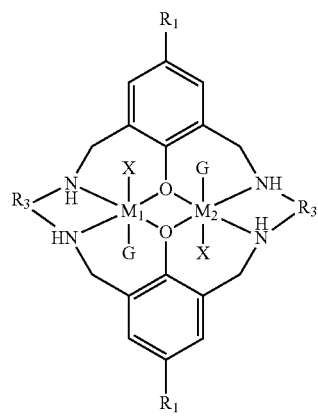

(Ic)

wherein:
Both occurrences of $R_1$ are the same, and are selected from halide, sulfoxide, silyl, and an optionally substituted alkyl, heteroalicyclic or alkoxy;
$R_3$ is selected from substituted or unsubstituted alkylenyl, cycloalkylenyl, alkenylenyl, heteroalkylenyl and arylenyl wherein alkylenyl, alkenylenyl, heteroalkylenyl, may optionally be interrupted by aryl, heteroaryl, alicyclic or heteroalicyclic;
Each X is the same, and is $OC(O)R^X$, $R^X$ is alkyl, alkenyl, heteroalkyl; or cycloalkyl;
Each G is not present; and
Both $M_1$ and $M_2$ are selected from Ni(II) or Ni(III)-X.

In a still more preferred embodiment, the catalyst of formula (I) has the formula (Id):

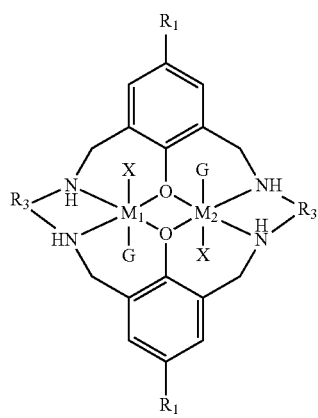

(Id)

Wherein:
Both occurrences of $R_1$ are the same, and are selected from t-butyl, methoxy, triethylsilyl, Br, $SO_2CH_3$, or piperidine;
$R_3$ is selected from 2,2-dimethylpropylenyl, —$CH_2$ $CH_2$ $CH_2$—, —$CH_2CH(CH_3)CH_2$—, —$CH_2C(CH_2C_6H_5)_2$ $CH_2$—, phenylene, —$CH_2$ $CH_2$—, —$CH_2$ $CH_2$ $CH_2$ $CH_2$—, —$CH_2$ $CH_2N$ $(CH_3)$ $CH_2$ $CH_2$—, 1,4-cyclohexandiyl, —$CH_2CH_2CH$ $(C_2H_5)$ or $CH_2C(C_2H_5)_2$ $CH_2$—;
Each X is the same, and is selected from OAc, $C_2CCF_3$, or $C_2C(CH_2)3Cy$;
Each G is not present; and
Both $M_1$ and $M_2$ are selected from Ni(II) or Ni(III)-X.

In a still more preferred embodiment, the catalyst of formula (I) has the formula (Ie):

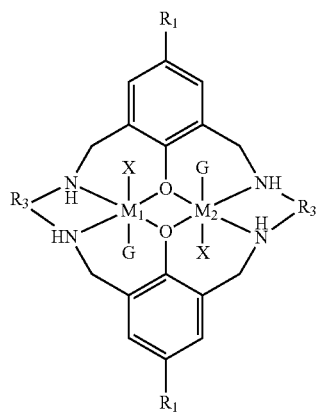

(Ie)

Wherein:
Both occurrences of $R_1$ are the same, and are selected from tBu or triethylsilyl;
$R_3$ is selected from 2,2-dimethylpropylenyl, —$CH_2$ $CH_2$ $CH_2$—, —$CH_2CH(CH_3)CH_2$—, —$CH_2C(CH_2C_6H_5)_2$ $CH_2$—, —$CH_2$ $CH_2$ $CH_2$ $CH_2$—, $CH_2C(C_2H_5)_2CH_2$ and —$CH_2CH_2CH$ $(C_2H_5)$—;
Each X is the same, and is selected from OAc, $C_2CCF_3$, or $C_2C(CH_2)3Cy$;
Each G is not present; and
Both $M_1$ and $M_2$ are selected from Ni(II) or Ni(III)-X.

In a still more preferred embodiment, the catalyst of formula (I) has the formula (If):

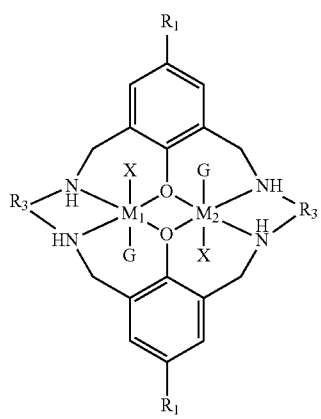

(If)

Wherein:

Both occurrences of $R_1$ are the same, and are tBu;

$R_3$ is selected from 2,2-dimethylpropylenyl, —$CH_2C(CH_2C_6H_5)_2CH_2$— and —$CH_2CH_2CH(C_2H_5)$—;

Each X is the same, and is OAc;

Each G is not present; and

Both $M_1$ and $M_2$ are selected from Ni(II) or Ni(III)-X.

The skilled person will appreciate that each of these preferred features can be taken in combination, mutatis mutandis. For example, $R_1$ is hydrogen, halide, silyl, silyl ether, sulfonyl, and optionally substituted alkyl or alkoxy; $R_3$ is selected from propylenyl, 2,2-dimethylpropylenyl, and substituted or unsubstituted phenylenyl or biphenylenyl; at least one of $M_1$ and $M_2$ is Ni(II) or Ni(III)-X, and the remaining $M_1$ or $M_2$ is selected from Mg(II), Zn(II), Ni(II) and Ni(III)-X (preferably both $M_1$ and $M_2$ are selected from Ni(II) and Ni(III)-X); X is $OC(O)R^X$, $OR^X$, halide, alkyl, aryl, heteroaryl, phosphinate or $OSO_2R^X$; $R^X$ is alkyl, alkenyl, alkynyl, heteroalkyl, aryl, heteroaryl or alkylaryl; and G may be present or absent (preferably G is absent).

Exemplary catalysts of the first aspect are as follows:

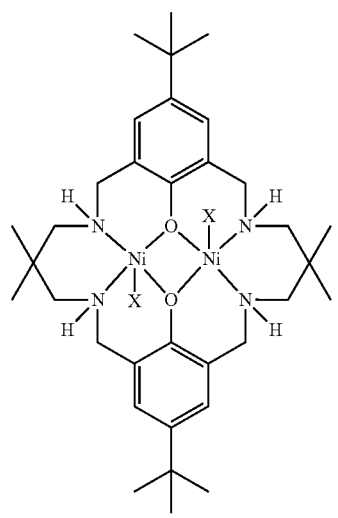

X = OAc
[L¹Ni₂(OAc)₂]

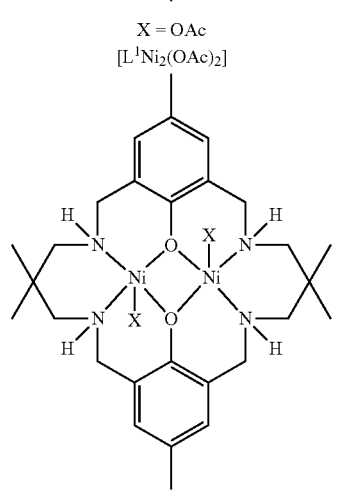

X = OAc
[L²Ni₂(OAc)₂]

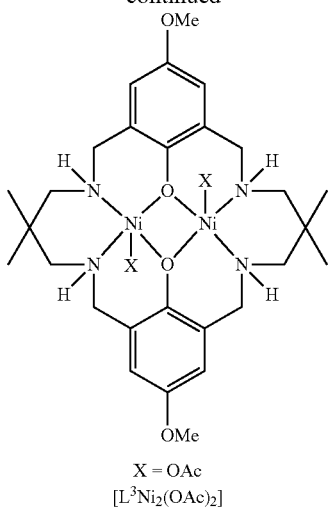

X = OAc
[L³Ni₂(OAc)₂]

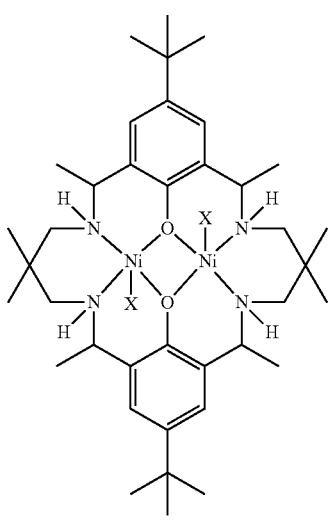

X = OAc
[L⁴Ni₂(OAc)₂]

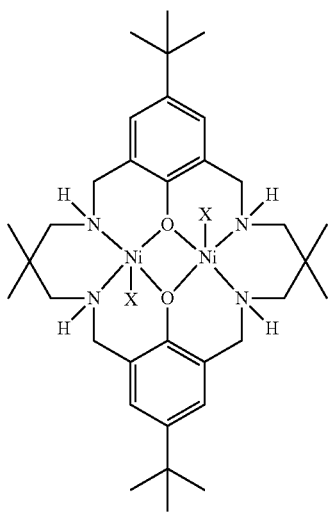

X = O₂CCF₃
[L¹Ni₂(O₂CCF₃)₂]

-continued
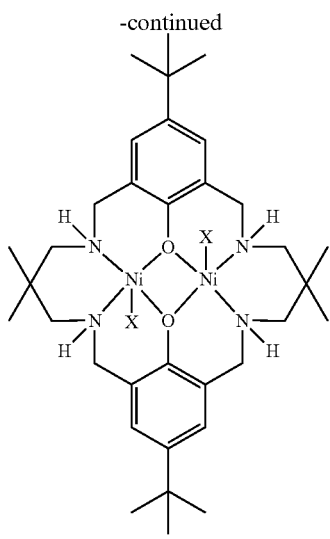
X = O₂C(CH₂)₃Cy
[L¹Ni₂(O₂C(CH₂)₃Cy)₂]
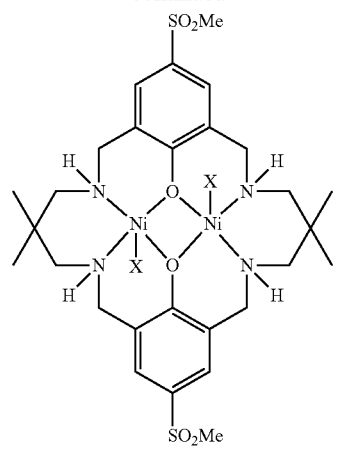
X = OAc
[L⁷Ni₂(OAc)₂]
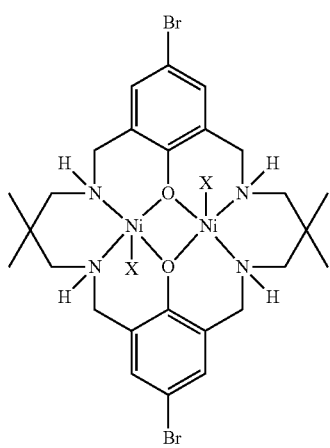
X = OAc
[L⁵Ni₂(OAc)₂]
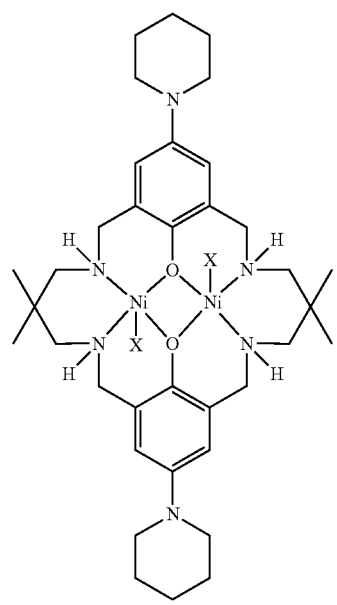
X = OAc
[L⁶Ni₂(OAc)₂]
X = OAc
[L⁸Ni₂(OAc)₂]

-continued
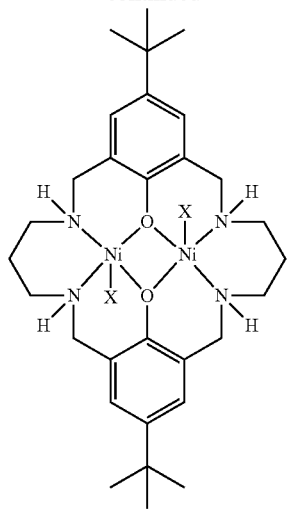
X = OAc
[L⁹Ni₂(OAc)₂]
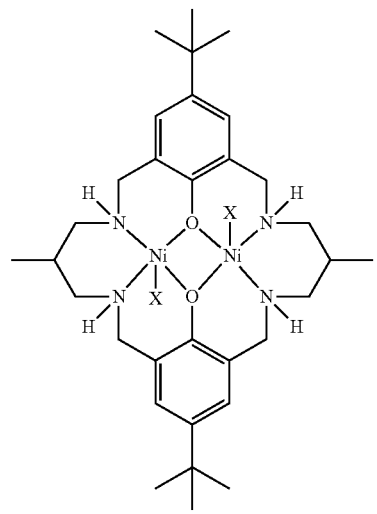
X = OAc
[L¹⁰Ni₂(OAc)₂]
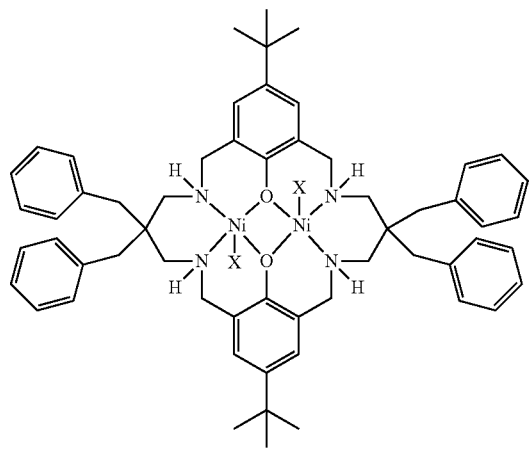
X = OAc
[L¹¹Ni₂(OAc)₂]
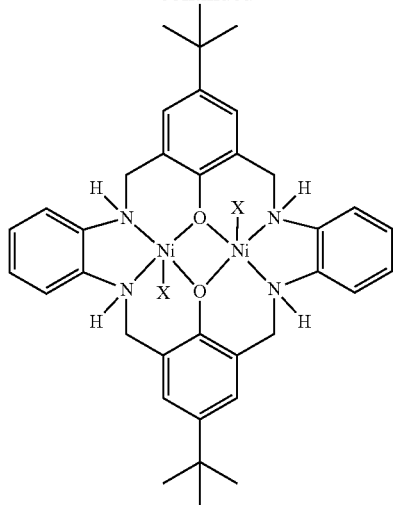
X = OAc
[L¹²Ni₂(OAc)₂]
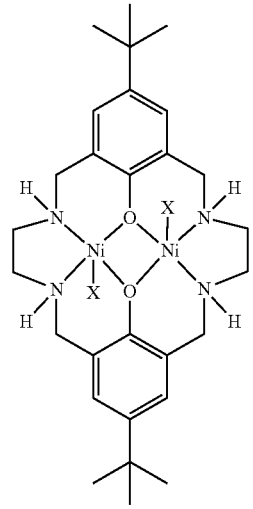
X = OAc
[L¹³Ni₂(OAc)₂]
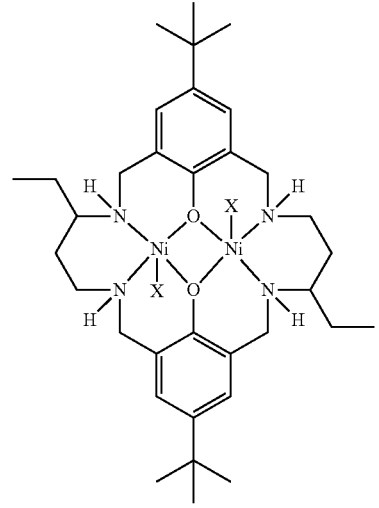
X = OAc
[L¹⁴Ni₂(OAc)₂]

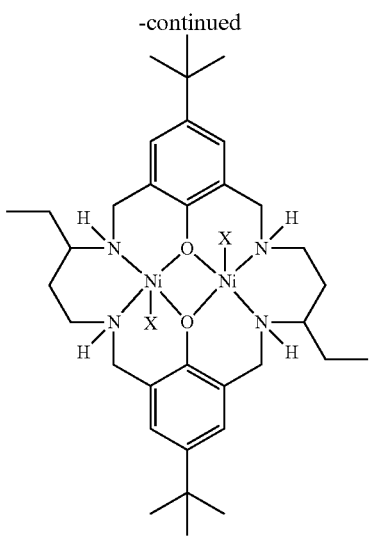

X = O₂CCF₃
[L¹⁴Ni₂(O₂CCF₃)₂]

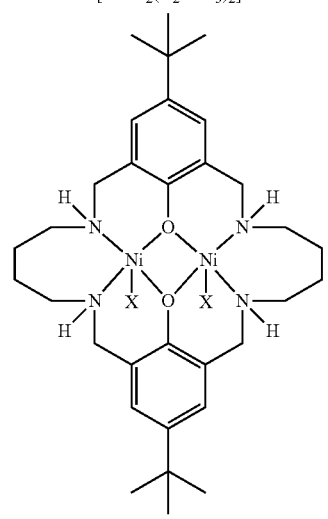

X = OAc
[L¹⁵Ni₂(OAc)₂]

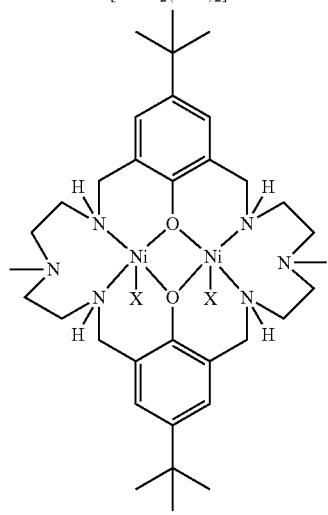

X = OAc
[L¹⁶Ni₂(OAc)₂]

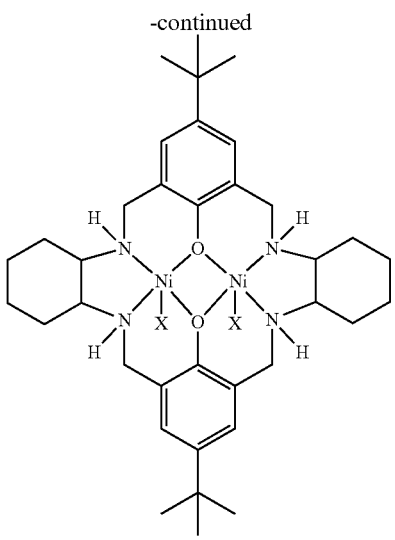

X = OAc
[L¹⁷Ni₂(OAc)₂]

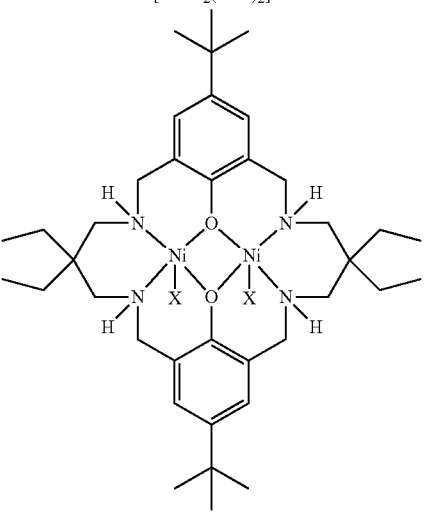

X = OAc
[L¹⁸Ni₂(OAc)₂]

The catalysts of the first aspect are capable of polymerising (i) carbon dioxide and an epoxide, (ii) an epoxide and an anhydride, and (iii) a lactide and/or a lactone. Therefore, in a second aspect of the invention there is provided a process for the reaction of carbon dioxide with an epoxide, an anhydride with an epoxide, or a lactide and/or a lactone in the presence of a catalyst according to the first aspect.

The process of the second aspect may be carried out in the presence of a chain transfer agent. Suitable chain transfer agents include the chain transfer agents, for example as defined by formula (II), in WO 2013/034750, the entire contents of which are hereby incorporated by reference. For example, the chain transfer agent may be water, or may comprise at least one amine (—NHR), alcohol (—OH), carboxylic acid (CO₂H) or thiol (—SH) moiety.

Examples of chain transfer agents useful in the second aspect include water, mono-alcohols (i.e. alcohols with one OH group, for example, 4-ethylbenzenesulfonic acid, methanol, ethanol, propanol, butanol, pentanol, hexanol, phenol, cyclohexanol), diols (for example, 1,2-ethanediol, 1-2-propanediol, 1,3-propanediol, 1,2-butanediol, 1-3-butanediol, 1,4-butanediol, 1,5-pentanediol, 1,6-hexanediol, 1,2-diphenol, 1,3-diphenol, 1,4-diphenol, catechol and cyclohexenediol), triols (glycerol, benzenetriol, 1,2,4-butanetriol, tris(methylalcohol)propane, tris(methylalcohol)ethane, tris(methylalcohol)nitropropane, trimethylolpropane, preferably glycerol or benzenetriol), tetraols (for example, calix[4]arene, 2,2-bis(methylalcohol)-1,3-propanediol, di(trimethylolpropane)), polyols (for example, dipentaerythritol, D-(+)-glucose or D-sorbitol), dihydroxy terminated polyesters (for example polylactic acid), dihydroxy terminated polyethers (for example poly(ethylene glycol)), acids (such as diphenylphosphinic acid), starch, lignin, monoamines (i.e. methylamine, dimethylamine, ethylamine, diethylamine, propylamine, dipropylamine, butylamine, dibutylamine, pentylamine, dipentylamine, hexylamine, dihexylamine), diamines (for example 1,4-butanediamine), triamines, diamine terminated polyethers, diamine terminated polyesters, mono-carboxylic acids (for example, 3,5-di-tert-butylbenzoic acid), dicarboxylic acids (for example, maleic acid, malonic acid, succinic acid, glutaric acid or terephthalic acid, preferably maleic acid, malonic acid, succinic acid, glutaric acid), tricarboxylic acids (for example, citric acid, 1,3,5-benzenetricarboxylic acid or 1,3,5-cyclohexanetricarboxylic acid, preferably citric acid), mono-thiols, dithoils, trithiols, and compounds having a mixture of hydroxyl, amine, carboxylic acid and thiol groups, for example lactic acid, glycolic acid, 3-hydroxypropionic acid, natural amino acids, unnatural amino acids, monosaccharides, disaccharides, oligosaccharides and polysaccharides (including pyranose and furanose forms). Preferably, the chain transfer agent is selected from cyclohexene diol, 1,2,4-butanetriol, tris(methylalcohol)propane, tris(methylalcohol)nitropropane, tris(methylalcohol)ethane, tri(methylalcohol)propane, tri(methylalcohol)butane, pentaerythritol, poly(propylene glycol), glycerol, mono- and diethylene glycol, propylene glycol, 2,2-bis (methylalcohol)-1,3-propanediol, 1,3,5-benzenetricarboxylic acid, 1,3,5-cyclohexanetricarboxylic acid, 1,4-butanediamine, 1,6-hexanediol, D-sorbitol, 1-butylamine, terephthalic acid, D-(+)-glucose, 3,5-di-tert-butylbenzoic acid, and water.

The process of the second aspect may be carried out in the presence of a solvent. Examples of solvents useful in the third aspect include toluene, diethyl carbonate, dimethyl carbonate, dioxane, dichlorobenzene, methylene chloride, propylene carbonate, ethylene carbonate, acetone, ethyl acetate, tetrahydrofuran (THF), etc.

When the process of the second aspect involves the reaction of an epoxide, the epoxide may be any compound comprising an epoxide moiety.

Preferably the epoxide is ethylene oxide, propylene oxide, butylene oxide or cyclohexene oxide. More preferably the epoxide is propylene oxide.

In a preferred embodiment of the second aspect of the invention, there is provided a process for the reaction of carbon dioxide with ethylene oxide, butylene oxide, cyclohexane oxide or propylene oxide, more preferably propylene oxide, an anhydride with ethylene oxide, butylene oxide, cyclohexene oxide or propylene oxide, more preferably propylene oxide, or a lactide and/or a lactone in the presence of a catalyst according to the first aspect.

Preferably, in the preferred embodiment of the second aspect, the catalyst of the first aspect is any one of those listed above as exemplary.

The epoxide may be purified (for example by distillation, such as over calcium hydride) prior to reaction with carbon dioxide or the anhydride. For example, the epoxide may be distilled prior to being added to the reaction mixture comprising the catalyst or catalyst system.

The process of the second aspect of the invention may be carried out at a pressure of 1 to 100 atmospheres, preferably at 1 to 40 atmospheres, such as at 1 to 20 atmospheres, more preferably at 1 or 10 atmospheres. The catalysts used in the process of the second aspect allow the reaction to be carried out at low pressures.

The process of the second aspect of the invention may be carried out at a temperature of about 0° C. to about 250° C., preferably from about 40° C. to about 160° C., even more preferably from about 50° C. to about 120° C. The duration of the process may be up to 168 hours, such as from about 1 minute to about 24 hours, for example from about 5 minutes to about 12 hours, e.g. from about 1 to about 6 hours.

The process temperature, for copolymerisations of carbon dioxide and an epoxide, may be used to control the product composition. When the temperature of the process of the second aspect which involves reacting carbon dioxide and an epoxide is increased, the selectivity of the catalyst towards the formation of cyclic carbonate is also increased. The catalysts and processes may operate at temperatures up to 250° C.

The process of the second aspect of the invention may be carried out at low catalytic loading. For example, when the reaction involves copolymerisation of carbon dioxide and an epoxide, the catalytic loading for the process is preferably in the range of 1:1,000-100,000 catalyst:epoxide, more preferably in the region of 1:1,000-300,000 catalyst:epoxide, even more preferably in the region of 1:10,000-100,000, and most preferably in the region of 1:50,000-100,000 catalyst:epoxide. When the process involves copolymerisation of an epoxide and an anhydride, or the reaction of a lactide and/or lactone, the catalytic loading for the process is preferably in the range of 1:1,000-300,000 catalyst: total monomer content, more preferably in the region of 1:10,000-100,000 catalyst: total monomer content, even more preferably in the region of 1:50,000-100,000 catalyst:total monomer content. The ratios above are molar ratios.

The catalysts of the first aspect, and in particular catalysts wherein both $M_1$ and $M_2$ are selected from Ni(II) and Ni(III)-X, have high activity and selectivity for producing polycarbonates by reacting carbon dioxide and an epoxide, optionally in the presence of a chain transfer agent, and preferably at temperatures between about 40° C. to about 160° C. Thus, the reaction times for the process of the second aspect can be less than 12 hours, and preferably from about 2 to about 6 hours. In particular, catalysts of the invention have improved activity in relation to di-substituted meso-epoxides (e.g. cyclohexene oxide) and mono-substituted epoxides (e.g.propylene oxide), and furthermore improved selectivity to mono-substituted epoxide reactants. The process of the second aspect can be carried out in a batch reactor or a continuous reactor.

It will be appreciated that the various features described above for the process of the second aspect may be present in combination mutatis mutandis. All preferred features of the first aspect apply equally to the second aspect and may be present in combination mutatis mutandis.

The third aspect of the invention provides a product of the process of the second aspect of the invention. All preferred features of the second aspect of the invention apply to the third aspect of the invention mutatis mutandis.

When the process of the second aspect is carried out in the presence of a chain transfer agent, it produces polymer chains which are terminated at substantially all ends with hydroxyl groups (i.e. polycarbonate polyols or polyester polyols). By "substantially", it is meant that at least 90% of the resultant polymer chains, preferably at least 95% of the resultant polymer chains, and even more preferably at least 98%, and even more preferably at least about 99% of the resultant polymer chains are terminated at all ends in hydroxyl groups. In order for at least 90% of the resultant polymer chains to be terminated at all ends with hydroxyl groups, it is preferred for the process of the second aspect to be carried out in the presence of at least about 4 equivalents of chain transfer agent, relative to the amount of catalyst. In order for at least 95% of the resultant polymer chains to be terminated at all ends with hydroxyl groups, it is preferred for the process of the second aspect to be carried out in the presence of at least about 10 equivalents of chain transfer agent, relative to the amount of catalyst. In order for at least 98% of the resultant polymer chains to be terminated at all ends with hydroxyl groups, it is preferred for the process of the second aspect to be carried out in the presence of at least about 20 equivalents of chain transfer agent, relative to the amount of catalyst. Thus, polyols obtained by the process of the second aspect are considered to form part of the third aspect of the invention.

The chain transfer agent referred to in the second aspect may be used to control the molecular weight ($M_n$) of the polymer products produced by the second aspect. Preferably, the molecular weight ($M_n$) of the polymer products of the third aspect is greater than about 200 g/mol. The molecular weight ($M_n$) of the polymer products of the third aspect may be from about 200 g/mol to about 200,000 g/mol. The molecular weight of the polymers produced by the third aspect can be measured by Gel Permeation Chromatography (GPC) using, for example, a GPC-60 manufactured by Polymer Labs, using THF as the eluent at a flow rate of 1 ml/min on Mixed B columns, manufactured by Polymer Labs. Narrow molecular weight polystyrene standards can be used to calibrate the instrument.

It is possible to produce polycarbonate polyols and polyester polyols having a $M_n$ of from about 200 g/mol to about 20,000 g/mol, preferably less than about 10,000 g/mol by adding a chain transfer agent to the process of the second aspect.

It is also possible to produce polymers having a $M_n$ of greater than about 20,000 g/mol from the process of the second aspect. Preferably, the polymer having a $M_n$ of greater than about 20,000 g/mol is a polycarbonate or a polyester, even more preferably a polycarbonate. Preferably, the polymer having a $M_n$ of greater than about 20,000 g/mol is a polycarbonate and is produced carrying out the process of the second aspect without adding a chain transfer agent (CTA).

The polymers produced by the second aspect may be produced to have a polydispersity index (PDI) of less than about 2, more preferably less than about 1.5, and even more preferably less than about 1.2. Furthermore, it is possible to control the molecular weight distribution so as to produce multi-modal or broad molecular weight distribution polymers by addition of one or more chain transfer agent(s).

The polymers produced by the process of the second aspect (e.g. polycarbonates such as PCHC or PPC), are useful building blocks in the preparation of various copolymeric materials. The polymers produced by the process of the second aspect may undergo further reaction, for example to produce polymeric products such as polyureas or polyamines. These processes and reactions are well known to the skilled person (for example, refer to WO2013/034750).

The polycarbonate or polyester polyols produced by the process of the second aspect may be used in various applications and products which conventionally use polyols, including (but not limited to) adhesives (such as hot melt adhesives and structural adhesives), a binder (such as forest product binders, foundry core binders and rubber crumb binders), coatings (such as powder coatings, transport, e.g. automotive or marine coatings, fast cure coatings, self-healing coatings, top coats and primers, varnishes, and coatings for marine applications, e.g. oil rigs), elastomers (such as cast elastomers, fibres/spandex elastomers, footwear elastomers, RIM/RRIM elastomers, synthetic leather elastomers, technical microcellular elastomers and TPU elastomers), flexible foams (such as viscoelastic foams), rigid foams (such as rigid and flexible panels, moulded rigid foams, aerosol gap filling foam, spray foams, refrigeration foams, pour-in-place foams, and foam slabs) and sealants (such as glazing sealants for commercial, industrial and transport (e.g. automotive) applications, and construction sealants). The polyamines and polyureas can be processed using methods standard techniques known in the art, such as foaming.

It will be understood that the polycarbonate and polyester polyols produced by the process of the second aspect may be mixed with other polyols prior to further use or reaction.

The polycarbonates, and in particular, polycarbonates having a $M_n$ of greater than about 20,000 g/mol (e.g. produced without adding chain transfer agent to the process of the second aspect) may have a number of beneficial properties including high strength, high toughness, high gloss, high transparency, low haze, high gas (e.g. oxygen and carbon dioxide) or water barrier properties, flame resistance, UV resistance, high durability, rigidity and stiffness, compatability with plasticizers, broad dimensional stability temperature, biodegradability and biocopatability, and modulus of elasticity and yield strength comparable to LDPE. Thus, these polymers may be used in various applications and products, such as electronic components, construction materials, data storage products, automotive and aircraft products, security components, medical applications, mobile phones, packaging (including bottles), optical applications (such as safety glass, windscreens, etc).

EXAMPLES

Example 1

Synthesis of Nickel-Containing Catalysts

Ligands $H_2L^{1-18}$ were synthesised by the method previously described by Kember et al, Angew. Chem. Int. Ed., 2009, 48, 931-933.

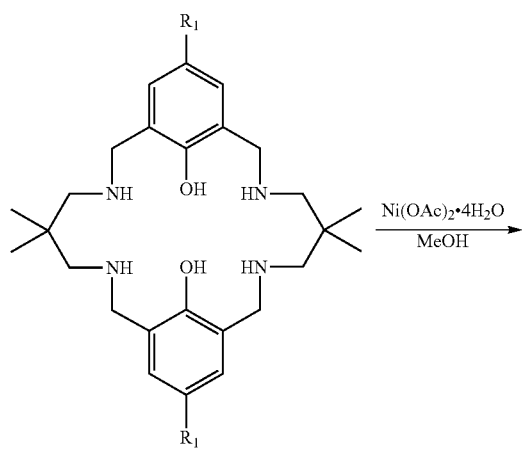

H₂L¹, R₁ = tBu
H₂L³, R₁ = OMe
H₂L⁵, R₁ = SiEt₃
H₂L⁶, R₁ = Br
H₂L⁷, R₁ = SO₂Me
H₂L⁸, R₁ = piperidine

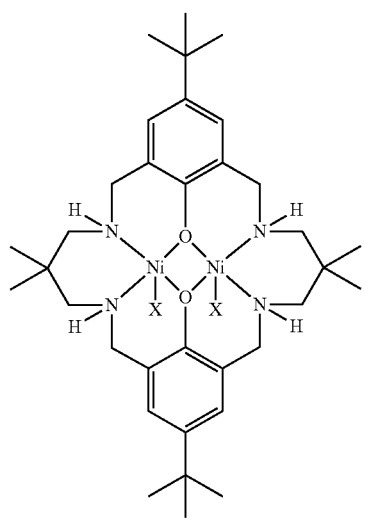

L¹Ni₂X₂
X = O₂CCF₃
X = O₂C(CH₂)₃Cy

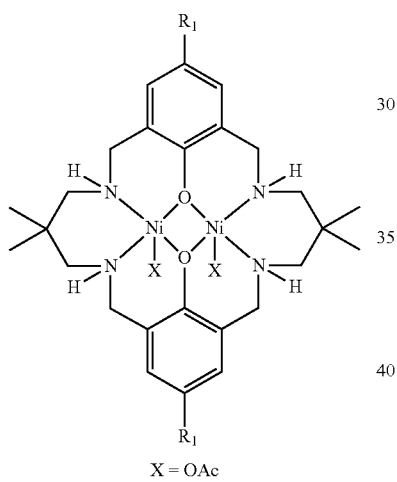

X = OAc

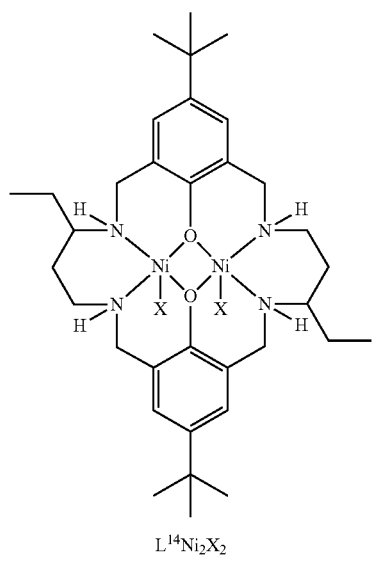

L¹⁴Ni₂X₂
X = O₂CCF₃

Ligands $H_2L^1$, $H_2L^{3'}$ $H_2L^5$, $H_2L^6$, $H_2$12 and $H_2L^8$ (2 mmol) were dissolved in MeOH (50 mL), Ni(OAc)₂·4H₂O (0.498 g, 4 mmol) was added portionwise over 15 minutes and the solution stirred overnight. The solvent was removed under vacuum and excess water/AcOH was removed by azeotrope with toluene (3×40 mL) to give a green or blue solid.

[L¹Ni₂(OAc)₂]: IR ($\upsilon_{C=O}$, cm⁻¹, neat): 1581 and 1413. MALDI-TOF MS: m/z: 727.6 ([M -OAc)]⁺, 100%);

[L³Ni₂(OAc)₂]: IR ($\upsilon_{C=O}$, cm⁻¹, neat): 1577 and 1413.

[L⁵Ni₂(OAc)₂]: IR ($\upsilon_{C=O}$, cm⁻¹, neat): 1585 and 1413. APCI-MS: m/z: 829 ([M-2 ⁻OAc+⁻O₂CH]⁺, 100%);

[L⁶Ni₂(OAc)₂]: IR ($\upsilon_{C=O}$, cm⁻¹, neat): 1577 and 1439. APCI-MS: m/z: 754 [M-2 ⁻OAc+⁻O₂CH]⁺, 100%);

[L⁷Ni₂(OAc)₂]: IR ($\upsilon_{C=O}$, cm⁻¹, neat): 1581 and 1413. APCI-MS: m/z: 757 ([M-2 ⁻OAc+⁻O₂CH]⁺, 100%).

[L⁸Ni₂(OAc)₂]: IR ($\upsilon_{C=O}$, cm⁻¹, neat): 1581 and 1413. APCI-MS: m/z: 779.2 ([M-⁻OAc]⁺, 75%), 765.2 ([M-2 ⁻OAC+⁻O₂CH]⁺, 95%).

Ligand $H_2L^x$ (2 mmol) was dissolved in MeOH (50 mL), Ni(X)₂·xH₂O (4 mmol) was added portionwise over 15 minutes and the solution stirred overnight. The solvent was removed under vacuum and excess water/acid was removed by azeotrope with toluene (3×40 mL) to give a green or blue solid.

[L¹Ni₂(C₂CCF₃)₂]: IR ($\upsilon_{C=O}$, cm⁻¹, neat): 1674 and 1480. ESI-MS: m/z =779.3 (100%, [M-O₂CCF₃]⁺).

[L¹Ni₂(C₂C(CH₂)₃Cy)₂]]: IR ($\upsilon_{C=O}$, cm⁻¹, neat): 1581 and 1406: ESI-MS: m/z=835.2 (100%, [M-(O₂C(CH₂)₃Cy)]⁺).

L¹⁴Ni₂(C₂CCF₃)₂: IR ($\upsilon_{C=O}$, cm⁻¹, neat): 1678 and 1480. ESI-MS: m/z: 711.2 ([M-2 ⁻ OAc+⁻O₂CH]⁺, 100%);

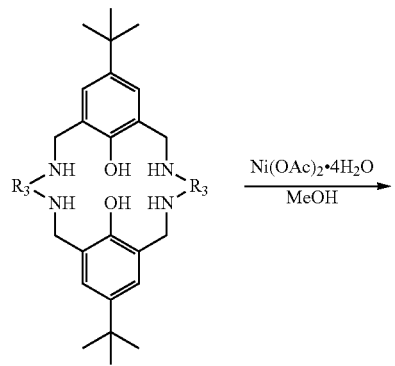

H$_2$L$^9$, R$_3$ = (CH$_2$)$_3$
H$_2$L$^{10}$, R$_3$ = CH$_2$CHMeCH$_2$
H$_2$L$^{11}$, R$_3$ = CH$_2$C(CH$_2$Ph)$_2$CH$_2$
H$_2$L$^{12}$, R$_3$ = phenylene (C$_6$H$_4$)
H$_2$L$^{13}$, R$_3$ = (CH$_2$)$_2$
H$_2$L$^{14}$, R$_3$ = CH$_2$CH$_2$CHEt
H$_2$L$^{15}$, R$_3$ = (CH$_2$)$_4$
H$_2$L$^{16}$, R$_3$ = (CH$_2$)$_2$NMe(CH$_2$)$_2$
H$_2$L$^{17}$, R$_3$ = 1,4-cyclohexane
H$_2$L$^{18}$, R$_3$ = CH$_2$CEt$_2$CH$_2$

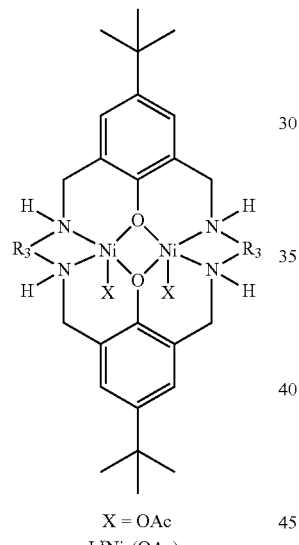

X = OAc
L$^x$Ni$_2$(OAc)$_2$

Ligand H$_2$L$^x$ (2 mmol) was dissolved in MeOH (50 mL), Ni(OAc)$_2$·4H$_2$O (0.498 g, 4 mmol) was added portionwise over 15 minutes and the solution stirred overnight. The solvent was removed under vacuum and excess water/acid was removed by azeotrope with toluene (3×40 mL) to give a green or blue solid.

L$^9$Ni$_2$(OAc)$_2$: IR ($\upsilon_{C=O}$, cm$^{-1}$, neat): 1573 and 1421. APCI-MS: m/z: 655.1 ([M-2 $^-$OAc+$^{-C}$$_2$CH]$^+$, 85%);

L$^{10}$Ni$_2$(OAc)$_2$: IR ($\upsilon_{C=O}$, cm$^{-1}$, neat): 1577 and 1421. APCI-MS: m/z: 685.1 ([M-2 $^-$OAc +$^{-C}$$_2$CH]$^+$, 70%);

L$^{11}$Ni$_2$(OAc)$_2$: IR ($\upsilon_{C=O}$, cm$^{-1}$, neat): 1581, 1413. APCI-MS: m/z: 1017.2 ([M-2 $^-$OAc +$^{-C}$$_2$CH]$^+$, 70%), 969.2 ([M-2 $^-$OAc]$^+$, 100%);

L$^{12}$Ni$_2$(OAc)$_2$: IR ($\upsilon_{C=O}$, cm$^{-1}$, neat): 1559 and 1417. APCI-MS: m/z: 725.1 ([M-2 $^-$OAc +$^{-C}$$_2$CH]$^+$, 50%);

L$^{13}$Ni$_2$(OAc)$_2$: IR ($\upsilon_{C=O}$, cm$^{-1}$, neat): 1551 and 1436. APCI-MS: m/z: 629.1 ([M-2 $^-$OAc +$^{-C}$$_2$CH]$^+$, 50%);

L$^{14}$Ni$_2$(OAc)$_2$: IR ($\upsilon_{C=O}$, cm$^{-1}$, neat): 1573 and 1410. APCI-MS: m/z: 725.2 ([M - $^-$OAc]$^+$, 100%).

L$^{15}$Ni$_2$(OAc)$_2$: IR ($\upsilon_{C=O}$, cm$^{-1}$, neat): 1566, 1413. APCI-MS: m/z: 685.1 ([M-2 $^-$OAc +$^{-C}$$_2$CH]$^+$, 100%);

L$^{16}$Ni$_2$(OAc)$_2$: IR ($\upsilon_{C=O}$, cm$^{-1}$, neat): 1577 and 1402. ESI-MS: m/z: 741.3 ([M-2 $^-$OAc +$^{-C}$$_2$CH]$^+$, 55%) ; 755.3 ([M-$^-$OAc]$^+$, 20%).

L$^{17}$Ni$_2$(OAc)$_2$: IR ($\upsilon_{C=O}$, cm$^{-1}$, neat): 1566, 1454. APCI-MS: m/z: 735.2 ([M-2 $^-$OAc +$^{-C}$$_2$CH]$^+$, 100%);

L$^{18}$Ni$_2$(OAc)$_2$: IR ($\upsilon_{C=O}$, cm$^{-1}$, neat): 1585, 1424. APCI-MS: m/z: 769.2 ([M - 2 $^-$OAc +$^{-C}$$_2$CH]$^+$, 95%);

Example 2

1 atm Copolymerisation of CHO with CO$_2$ Using Ni Catalysts

The catalyst (0.0247 or 0.00494 mmol) was added to a dried Schlenk tube and dried under vacuum for 30 minutes. CHO (2.5 mL, 24.7 mmol) was added under CO$_2$ via a syringe, the vessel was heated to 100° C. and stirred for 2-16 hours, after which the heating was removed and a sample taken for GPC/NMR analysis.

TABLE 1

Copolymerisation of CHO and CO$_2$ (1 atm) using Ni catalysts

| Catalyst | Time (h) | TON | TOF | CHO conversion | Selectivity (CHO) | Mn (g/mol) | PDI |
| --- | --- | --- | --- | --- | --- | --- | --- |
| [L$^1$Ni$_2$(OAc)$_2$] | 3 | 520 | 173.3 | 52 | 99.7 | 18000, 10400 | 1.02, 1.053 |
| [L$^1$Ni$_2$(O$_2$C(CH$_2$)Cy)$_2$] | 4 | 467 | 116.8 | 46.7 | 100 | 14100, 7600 | 1.019, 1.055 |
| [L$^1$Ni$_2$(O$_2$CCF$_3$)$_2$] | 3.25 | 562.5 | 173.1 | 56.25 | 100 | 18700 | 1.313 |
| [L$^8$Ni$_2$(OAc)$_2$] | 4 | 102.5 | 25.63 | 10.25 | 90.4 | 3300 | 1.225 |
| [L$^{11}$Ni$_2$(OAc)$_2$] | 4 | 441.5 | 110.4 | 44.15 | 100 | 15200, 7900 | 1.02, 1.086 |
| [L$^9$Ni$_2$(OAc)$_2$] | 16 | 594 | 37.13 | 59.4 | 99.6 | 25400, 15900, 8100 | 1.004, 1.018, 1.019 |
| [L$^{15}$Ni$_2$(OAc)$_2$] | 16 | 194.4 | 12.15 | 19.44 | 98.7 | 6200, 2800 | 1.034, 1.095 |
| [L$^{10}$Ni$_2$(OAc)$_2$] | 5 | 356 | 71.2 | 35.6 | 99.8 | 4300 | 1.197 |
| [L$^{14}$Ni$_2$(OAc)$_2$] | 3.5 | 562 | 160.6 | 56.2 | 99.7 | 20200, 8900 | 1.044, 1.107 |
| [L$^{18}$Ni2(OAc)2] | 2.75 | 534 | 194.4 | 53.4 | 99.9 | 7300 | 1.25 |

The catalysts show over 90% selectivity for polymer towards the reactant cyclohexene oxide, >99% selectivity for polycarbonate over polyether (that is >99% carbonate incorporation), high activities and activity under low pressures (1 atm).

Example 3

Polymerisation of $CO_2$ and PO at 90° C. and 0.21 mmol [$L^1Ni_2(OAc)_2$]

[$L^1Ni_2(OAc)_2$] (0.21 mmol) was dissolved in propylene oxide (214 mmol) in a Schlenk tube and the solution transferred into a pre-dried 100 mL stainless steel Parr pressure vessel using a syringe. The vessel was charged with $CO_2$ (3.0 MPa) and heated to 90° C. The solution was stirred mechanically for 6 hours, giving 7.5g of poly(propylene carbonate) (Mn 19000/9700, PDI 1.03/1.04) as a white solid with a high selectivity for polymer and >99% carbonate linkages.

Example 4

Polymerisation of $CO_2$ and PO at 80° C. and 0.11 mmol [$L^1Ni_2(OAc)_2$]

[$L^1Ni_2(OAc)_2$] (0.11 mmol) was dissolved in propylene oxide (214 mmol) in a Schlenk tube and the solution transferred into a pre-dried 100 mL stainless steel Parr pressure vessel using a syringe. The vessel was charged with $CO_2$ (4.0 MPa) and heated to 80° C. The solution was stirred mechanically for 16 hours, giving 7.4 g of poly(propylene carbonate) (Mn 23000/11400, PDI 1.03/1.05) as a white solid with a high selectivity for polymer and >99% carbonate linkages.

Example 5

Polymerisation of $CO_2$ and PO at 90° C. and 0.11 mmol of [$L^1Ni_2(OAc)_2$]

[$L^1Ni_2(OAc)_2$] (0.11 mmol) was dissolved in propylene oxide (214 mmol) in a Schlenk tube and the solution transferred into a pre-dried 100 mL stainless steel Parr pressure vessel using a syringe. The vessel was charged with $CO_2$ (4.0 MPa) and heated to 90° C. The solution was stirred mechanically for 17 hours, giving 11.5 g of poly(propylene carbonate) (Mn 39900/17600, PDI 1.03/1.09) as a white solid with a high selectivity for polymer and >99% carbonate linkages.

Example 6

Polymerisation of $CO_2$ and CHO at 100° C. and 0.05 mmol of [$L^1Ni_2(OAc)_2$]

[$L^1Ni_2(OAc)_2$] (0.05 mmol) was dissolved in cyclohexene oxide (50 mmol) in a Schlenk. The vessel was degassed, charged with $CO_2$ (0.1 MPa) and heated at 100° C. with magnetic stirring for 3 hours, giving 2.9g of poly(cyclohexene carbonate). The polymer contained >99% carbonate linkages and was produced with >99% selectivity (Mn 12000/5000, PDI 1.04/1.11).

Example 7

Polymerisation of $CO_2$ and CHO at 80° C. and 0.09 mmol of [$L^1Ni_2(OAc)_2$]

[$L^1Ni_2(OAc)_2$] (0.09 mmol) was dissolved in cyclohexene oxide (0.9 mmol) and propylene oxide (0.9 mmol) and the solution transferred into a pre-dried 100 mL stainless steel Parr pressure vessel using a syringe. The vessel was charged with $CO_2$ (1.5 MPa) and heated to 80° C. The solution was stirred mechanically for 7 hours, giving 13.1 g poly(cyclohexene-co-propylene) carbonate containing >99% carbonate linkages with a very high selectivity for polymer formation.

Example 8

Comparison of Polymerisation of $CO_2$ and PO with [$L^1Ni_2(OAc)_2$], [$L^5Ni_2(OAc)_2$], and [$L^1Mg_2(OAc)_2$] at a Range of Temperatures The catalyst ([$L^5Ni_2(OAc)_2$]/[$L^1Ni_2(OAc)_2$]/[$L^1Mg_2(OAc)_2$]) (0.21 mmol) was dissolved in propylene oxide (214 mmol) in a Schlenk tube and the solution transferred into a pre-dried 100 mL stainless steel Parr pressure vessel using a syringe. The vessel was charged with 0.4-0.5 MPa $CO_2$ pressure and heated to temperature. Once at temperature the $CO_2$ pressure was topped up to 4.0 MPa. The solution was stirred mechanically for the desired reaction time and the reaction followed by in-situ ATR-FT-IR spectroscopy. The selectivity and activity of the reaction was determined by ATR-FT-IR spectroscopy and confirmed with $^1H$ NMR spectroscopy of the crude product. Results are set out in FIG. 1 and FIG. 2.

FIG. 1 shows that the selectivity of the catalyst having a Magnesium centre [$L^1Mg_2(OAc)_2$] is much lower than compared with a catalyst having the same ligand structure but with a Nickel metal centre [$L^1Ni_2(OAc)_2$]. Furthermore, FIG. 1 shows that the selectivity of catalysts having nickel metal centres remains high over a broad temperature range, at 100C, the selectivity of the nickel centred catalysts, [$L^1Ni_2(OAc)_2$], [$L^5Ni_2(OAc)_2$], is still at least 55%, whereas at 100C the selectivity of the magnesium centred catalyst, [$L^1Mg_2(OAc)_2$], has fallen to 0%.

Figure 2:
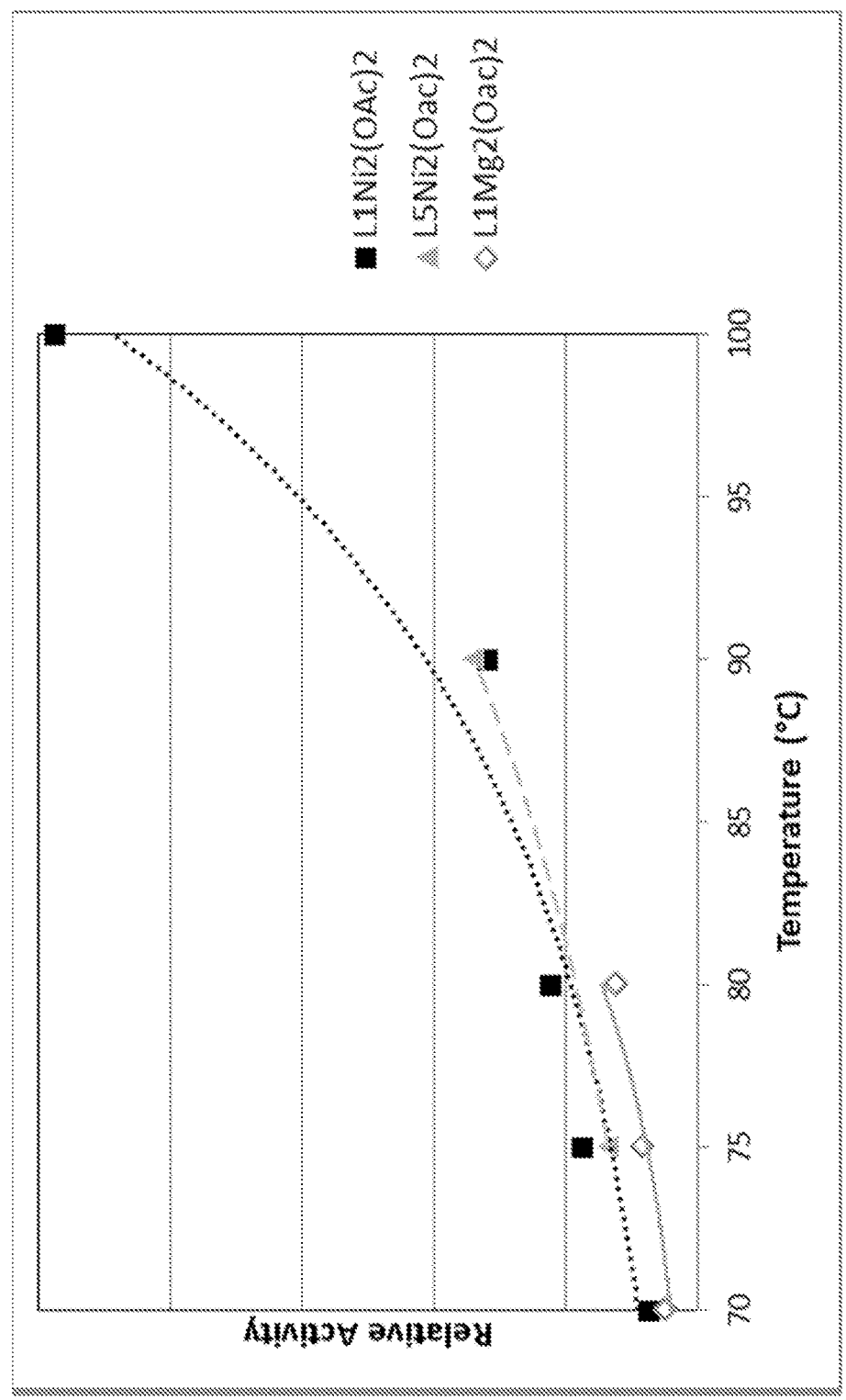
FIG. 2 shows the activity of various catalysts.

FIG. 2 shows that the activity of the catalyst having a Magnesium centre [$L^1Mg_2(OAc)_2$] is much lower than compared with a catalyst having the same ligand structure but with a Nickel metal centre [$L^1Ni_2(OAc)_2$] across a temperature range. Furthermore, FIG. 2 shows that the activity of the nickel centred catalyst significantly increases at higher temperature, whilst retaining selectivity for PPC, unlike the magnesium centred catalyst which shows less activity and no selectivity at higher temperatures (see FIG. 1).

Figure 3:
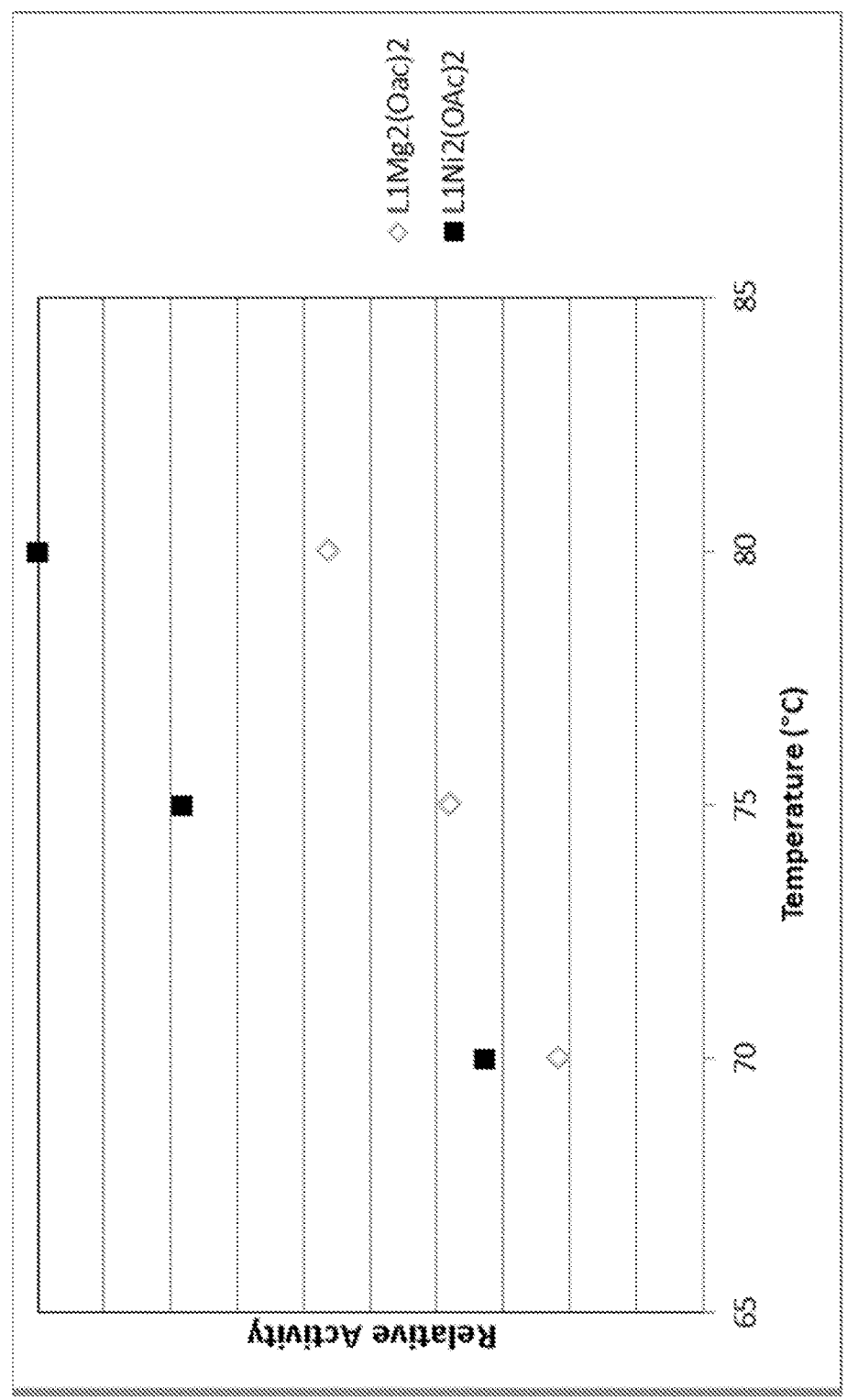
FIG. 3 is a close up from FIG. 2.

FIG. 3 is a close up from FIG. 2 in the window 65-85° C. and shows more closely the comparative activities of [$L^1Ni_2(OAc)_2$] and [$L^1Mg_2(OAc)_2$] in this temperature range. It demonstrates more clearly that [$L^1Ni_2(OAc)_2$] is surprisingly twice as active as it's magnesium analogue.

Example 9

Comparison of 1 atm Copolymerisation of CHO and CO2 with Equivalent Ni and Mg Complexes under Identical Conditions

TABLE 2

Comparison of catalytic activity of equivalent Ni and Mg complexes under identical conditions for CHO and $CO_2$ (1 atm) copolymerisation.

| cat. | Cat Loading | Time (h) | TON | TOF | Selectivity (CHO) |
|---|---|---|---|---|---|
| [$L^1Mg_2(OAc)_2$] | 1:1000 | 5 | 491 | 98 | 99.8 |
| [$L^1Ni_2(OAc)_2$] | 1:1000 | 3 | 520 | 173.3 | 99.7 |
| [$L^1Mg_2(OAc)_2$] | 1:5000 | 3 | 664 | 221 | 100 |
| [$L^1Ni_2(OAc)_2$] | 1:5000 | 3.25 | 997 | 325.7 | 100 |
| [$L^{14}Mg_2(OAc)_2$] | 1:1000 | 5 | 260 | 52 | 98.4 |
| [$L^{14}Ni_2(OAc)_2$] | 1:1000 | 3.5 | 562 | 160.6 | 99.7 |
| [$L^{11}Mg_2(OAc)_2$] | 1:1000 | 5 | 217.5 | 43.5 | 99.4 |
| [$L^{11}Ni_2(OAc)_2$] | 1:1000 | 4 | 441.5 | 110.4 | 100 |

The catalysts having nickel metal centres show over 99% selectivity to the reactant cyclohexene oxide. The catalysts having nickel metal centres also display a higher turnover number and a higher turnover frequency when compared to catalysts having the same ligand structure but with magnesium metal centres and when tested under identical reaction conditions. In particular, the turnover frequency of the catalysts having nickel metal centres is in some cases double that shown with catalysts having magnesium metal centres.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A catalyst of formula (I):

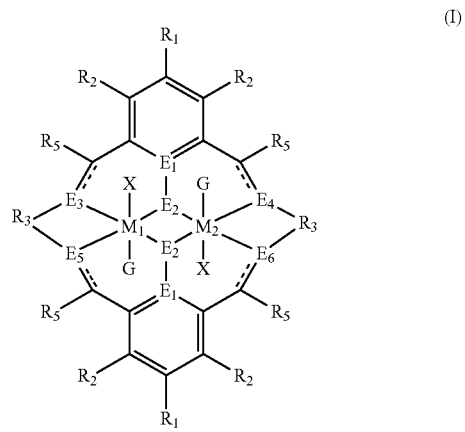

wherein:

$M_1$ and $M_2$ are independently selected from Zn(II), Cr(II), Co(II), Cu(II), Mn(II), Mg(II), Ni(II), Fe(II), Ti(II), V(II), Cr(III)-X, Co(III)-X, Mn(III)-X, Fe(III)-X, Ca(II), Ge(II), Al(III)-X, Ti(III)-X, V(III)-X, Ge(IV)-(X)$_2$ or Ti(IV)-(X)$_2$;

wherein at least one of $M_1$ or $M_2$ is selected from Ni(II) and Ni(III)-X;

$R_1$ and $R_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

$R_3$ is a 2,2-dialkylpropylenyl;

$R_5$ is independently selected from H, or optionally substituted aliphatic, heteroaliphatic, alicyclic, heteroalicyclic, aryl, heteroaryl, alkylheteroaryl or alkylaryl;

$E_1$ is C, $E_2$ is O, S or NH or $E_1$ is N and $E_2$ is O;

E3, E4, E5 and E6 are selected from N, NR$_4$, O and S, wherein when E3, E4, E5 or E6 are N, ===== is ══════, and wherein when E3, E4, E5 or E6 are NR$_4$, O or S, ===== is ─────;

$R_4$ is independently selected from hydrogen, or optionally substituted aliphatic, heteroaliphatic, alicyclic, heteroalicyclic, aryl, heteroaryl, alkylheteroaryl or alkylaryl;

X is independently selected from OC(O)R$^x$, OSO$_2$R$^x$, OSOR$^x$, OSO(R$^x$)$_2$, S(O)R$^x$, OR$^x$, phosphinate, halide, nitrate, hydroxyl, carbonate, amino, nitro, amido or optionally substituted aliphatic, heteroaliphatic, alicyclic, heteroalicyclic, aryl or heteroaryl;

$R_x$ is independently hydrogen, or optionally substituted aliphatic, haloaliphatic, heteroaliphatic, alicyclic, heteroalicyclic, aryl, alkylaryl or heteroaryl; and G is absent or independently selected from a neutral or anionic donor ligand which is a Lewis base.

2. The catalyst of claim 1, wherein at least one of $M_1$ or $M_2$ is Ni(II).

3. The catalyst of claim 1, wherein one of $M_1$ or $M_2$ is selected from Ni(II) and Ni(III)-X and the remaining occurrence of $M_1$ and $M_2$ is selected from Zn(II), Cr(III)-X, Cu(II), Co(III)-X, Co(II), Cu(II), Mn(III)-X, Mn(II), Mg(II), Ni(II), Ni(III)-X, Fe(II), Fe(III)-X, Ti(II), Ti(III)-X, V(II), V(III)-X, Ge(IV)-(X)$_2$ and Ti(IV)-(X)$_2$.

4. The catalyst of claim 3, wherein the remaining occurrence of M$_1$ and M$_2$ is selected from Zn(II), Cr(III)-X, Co(II), Cu(II), Mn(II), Mg(II), Ni(II), Ni(III)-X, Fe(II), Fe(III)-X and V(II).

5. The catalyst of claim 3, wherein the remaining occurrence of M$_1$ and M$_2$ is selected from Zn(II), Cr(III)-X, Co(II), Mn(II), Mg(II), Ni(II), Ni(III)-X, Fe(II), and Fe(III)-X.

6. The catalyst of claim 3, wherein the remaining occurrence of M$_1$ and M$_2$ is selected from any of: Zn(II), Mg(II), Ni(II), Co(II), Co(III)-X and Ni(III)-X.

7. The catalyst of claim 1, wherein both M$_1$ and M$_2$ are Ni(II).

8. A catalyst of formula (I):

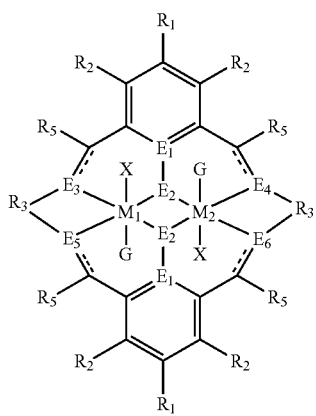

wherein:
M$_1$ and M$_2$ are independently selected from Zn(II), Cr(II), Co(II), Cu(II), Mn(II), Mg(II), Ni(II), Fe(II), Ti(II), V(II), Cr(III)-X, Mn(III)-X, Ni(III)-X, Fe(III)-X, Ca(II), Ge(II), Al(III)-X, Ti(III)-X, Ge(IV)-(X)$_2$ or Ti(IV)-(X)$_2$;
wherein at least one of M$_1$ or M$_2$ is selected from Ni(II) and Ni(III)-X;
R$_1$ and R$_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;
R$_3$ is independently selected from a 2,2-dimethylpropylenyl, —CH$_2$C(CH$_2$C$_6$H$_5$)$_2$CH$_2$—, —CH$_2$C(C$_2$H$_5$)$_2$CH$_2$— and —CH$_2$CH$_2$CH (C$_2$H$_5$)—;
R$_5$ is independently selected from H, or optionally substituted aliphatic, heteroaliphatic, alicyclic, heteroalicyclic, aryl, heteroaryl, alkylheteroaryl or alkylaryl;
E$_1$ is C, E$_2$ is O, S or NH or E$_1$ is N and E$_2$ is O;
E3, E4, E5 and E6 are selected from N, NR$_4$, O and S, wherein when E3, E4, E5 or E6 are N, ------ is ══, and wherein when E3, E4, E5 or E6 are NR$_4$, O or S, ------ is ──;
R$_4$ is independently selected from hydrogen, or optionally substituted aliphatic, heteroaliphatic, alicyclic, heteroalicyclic, aryl, heteroaryl, alkylheteroaryl or alkylaryl;

X is independently selected from OC(O)R$^x$, OSO$_2$R$^x$, OSOR$^x$, OSO(R$^x$)$_2$, S(O)R$^x$, OR$^x$, phosphinate, halide, nitrate, hydroxyl, carbonate, amino, nitro, amido or optionally substituted aliphatic, heteroaliphatic, alicyclic, heteroalicyclic, aryl or heteroaryl;
R$_x$ is independently hydrogen, or optionally substituted aliphatic, haloaliphatic, heteroaliphatic, alicyclic, heteroalicyclic, aryl, alkylaryl or heteroaryl; and
G is absent or independently selected from a neutral or anionic donor ligand which is a Lewis base.

9. A process for a reaction of:
a. carbon dioxide with an epoxide;
b. an epoxide and an anhydride; and/or
c. a lactide and/or a lactone, in the presence of the catalyst of claim 8.

10. The catalyst of claim 9, wherein R$_3$ is selected from substituted or unsubstituted alkylene and substituted or unsubstituted arylene.

11. The catalyst of claim 9, wherein R$_3$ is selected from substituted or unsubstituted alkylene, alkenylene, alkynylene, heteroalkylene, heteroalkenylene, heteroalkynylene, arylene, and cycloalkylene.

12. The catalyst of claim 9, wherein R$_3$ is selected from 2,2-dimethylpropylenyl, —CH$_2$ CH$_2$ CH$_2$—, —CH$_2$CH (CH$_3$)CH$_2$—, —CH$_2$C(CH$_2$C$_6$H$_5$)$_2$CH$_2$—, phenylene, —CH$_2$ CH$_2$—, —CH$_2$ CH$_2$ CH$_2$ CH$_2$—, —CH$_2$ CH$_2$N (CH$_3$) CH$_2$ CH$_2$—, 1,4-cyclohexandiyl, —CH$_2$CH$_2$CH (C$_2$H$_5$)— or —CH$_2$C(C$_2$H$_5$)$_2$CH$_2$—.

13. The catalyst of claim 9, wherein R$_3$ is selected from is selected from 2,2-dimethylpropylenyl, —CH$_2$ CH$_2$ CH$_2$—, —CH$_2$CH(CH$_3$)CH$_2$—, —CH$_2$C(CH$_2$C$_6$H$_5$)$_2$ CH$_2$—, —CH$_2$CH$_2$CH (C$_2$H$_5$)—, —CH$_2$ CH$_2$ CH$_2$ CH$_2$—.

14. The catalyst of claim 1, wherein both occurrences of R$_3$ are the same.

15. The catalyst of claim 1, wherein E$_1$ is C and E$_2$ is O, S, or NH.

16. The catalyst of claim 1, wherein E3, E4, E5 and E6 are NR$_4$.

17. The catalyst of claim 1, wherein R$_4$ is selected from hydrogen or an optionally substituted alkyl, alkenyl, alkynyl, heteroalkyl, heteroalkenyl, heteroalkynyl, aryl or heteroaryl.

18. The catalyst of claim 1, wherein each occurrence of R$_4$ is the same.

19. The catalyst of claim 1, wherein E3, E4, E5 and E6 are the same.

20. The catalyst of claim 1, wherein R$_1$ is selected from hydrogen, halide, amino, nitro, sulfoxide, sulfonyl, sulfinate, silyl, silyl ether, and optionally substituted alkyl, alkenyl, aryl, heteroaryl, alkoxy, aryloxy, arylthio or alkylthio.

21. The catalyst of claim 1, wherein R$_1$ is selected from halide, sulfoxide, silyl, and an optionally substituted alkyl, heteroaryl or alkoxy.

22. The catalyst of claim 1, wherein R$_1$ is selected from t-butyl, methoxy, triethylsilyl, bromide, SO$_2$CH$_3$, or piperidinyl.

23. The catalyst of claim 22, wherein R$_1$ is selected from t-butyl or triethylsilyl.

24. The catalyst of claim 1, wherein both occurrences of R$_1$ are the same.

25. The catalyst of claim 1, wherein X is selected from OC(O)R$^x$, OSO$_2$R$^x$, OS(O)R$^x$, OSO(R$^x$)$_2$, S(O)R$^x$, OR$^x$, phosphinate, halide, nitrate, hydroxyl, carbonate, amino, nitro, amido, and optionally substituted alkyl, heteroalkyl, alicyclic, heteroalicyclic, aryl or heteroaryl.

26. The catalyst of claim 1, wherein X is selected from OC(O)R$^x$, OR$^x$, halide, carbonate, amino, nitro, alkyl, aryl, heteroaryl, phosphinate or OSO$_2$R$^x$.

27. The catalyst of claim 1, wherein X is selected from OC(O)R$^x$, OR$^x$, halide, alkyl, aryl, heteroaryl, phosphinate or OSO$_2$R$^x$.

28. The catalyst of claim 1, wherein X is OC(O)R$^x$.

29. The catalyst of claim 1, wherein X is selected from OAc, O$_2$CCF$_3$, or C$_2$C(CH$_2$)3Cy.

30. The catalyst of claim 1, wherein both occurrences of X are the same.

31. The catalyst of claim 1, wherein R$^x$ is an optionally substituted alkyl, alkenyl, alkynyl, heteroalkyl, aryl, heteroaryl, cycloalkyl or alkylaryl.

32. The catalyst of claim 1, wherein R$^x$ is selected from hydrogen, or an optionally substituted aliphatic, haloaliphatic, heteroaliphatic, alicyclic, heteroalicyclic, aryl, alkylaryl or heteroaryl.

33. The catalyst of claim 1, wherein R$^x$ is selected from an optionally substituted alkyl, alkenyl, heteroalkyl, or cycloalkyl.

34. The catalyst of claim 1, wherein R$^x$ is selected from an optionally substituted alkyl, heteroalkyl, or cycloalkyl.

35. The catalyst of claim 1, wherein R$^x$ is an optionally substituted alkyl.

36. The catalyst of claim 1, wherein both occurrences of R$^x$ are the same.

37. The catalyst of claim 1, wherein each occurrence of R$_2$ and R$_5$ is hydrogen.

38. The catalyst of claim 1, wherein both occurrences of R$_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio;

R$_2$ is hydrogen;

both occurrences of R$_3$ are the same, and are a 2,2-dialkylpropylene;

E$_1$ is C and E$_2$ is O;

E3, E4, E5 and E6 are NR$_4$;

R$_4$ is hydrogen;

each X is the same, and is selected from OC(O)R$^x$, OR$^x$, halide, carbonate, amino, nitro, alkyl, aryl, heteroaryl, phosphinate or OSO$_2$R$^x$, each R$^x$ is the same and is selected from alkyl, alkenyl, alkynyl, heteroalkyl, aryl, heteroaryl or alkylaryl;

each G, where present, is the same and is selected from halide; water; a heteroaryl optionally substituted by alkyl, alkenyl, alkynyl, alkoxy, halogen, hydroxyl, nitro or nitrile; and one of M$_1$ and M$_2$ is Ni(II) or Ni(III)-X, and the remaining M$_1$ or M$_2$ is selected from Mg(II), Zn(II), Cr(III)-X, Co(II), Co-(III)-X Mn(II), Ni(II), Ni(III)-X, Fe(II), and Fe(III)-X.

39. The catalyst of claim 38, wherein both occurrences of M$_1$ and M$_2$ are selected from Ni(II) and Ni(III)-X.

40. The catalyst of claim 38, wherein R$_1$ is hydrogen, halide, silyl, silyl ether, sulfonyl or optionally substituted alkyl or alkoxyl.

41. The catalyst of claim 1, of the formula (Ib):

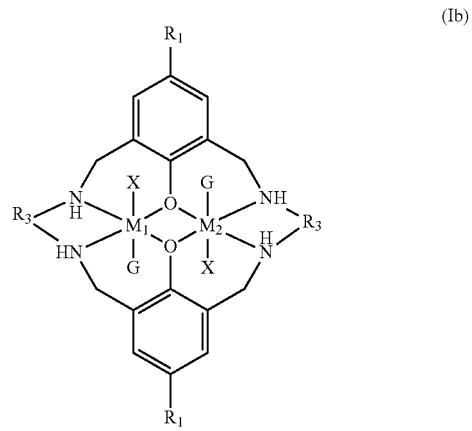

wherein:

both occurrences of R$_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio;

R$_3$ is 2,2-dialkylpropylenyl;

each X is the same, and is selected from OC(O)R$^x$, OR$^x$, halide, carbonate, amino, nitro, alkyl, aryl, heteroaryl, phosphinate or OSO$_2$R$^x$, R$^x$ is alkyl, alkenyl, alkynyl, heteroalkyl, aryl, heteroaryl or alkylaryl;

R$^x$ is alkyl, alkenyl, alkynyl, heteroalkyl, aryl, heteroaryl or alkylaryl;

each G, where present, is independently selected from halide; water; a heteroaryl optionally substituted by alkyl, alkenyl, alkynyl, alkoxy, halogen, hydroxyl, nitro or nitrile; and one occurrence of M$_1$ and M$_2$ is Ni(II) or Ni(III)-X, and the remaining occurrence of M$_1$ or M$_2$ is selected from Mg(II), Zn(II), Cr(III)-X, Co(II), Co(III)-X, Mn(II), Ni(II), Ni(III)-X, Fe(II), and Fe(III)-X.

42. The catalyst of claim 41, wherein R$_1$ is hydrogen, halide, silyl, silyl ether, sulfonyl, and optionally substituted alkyl or alkoxy.

43. The catalyst of claim 41, wherein R$_3$ is 2,2-dimethylpropylenyl.

44. The catalyst of claim 41, wherein M$_1$ and M$_2$ are selected from Ni(II) and Ni(III)-X.

45. The catalyst of claim 41, wherein X is OC(O)R$^x$, OR$^x$, halide, alkyl, aryl, heteroaryl, phosphinate or OSC$_2$R$^x$.

46. The catalyst of claim 41, wherein R$^x$ is alkyl, alkenyl, alkynyl, heteroalkyl, aryl, heteroaryl, or alkylaryl.

47. The catalyst of claim 41, wherein G is absent.

48. The catalyst of claim 1 of the formula:
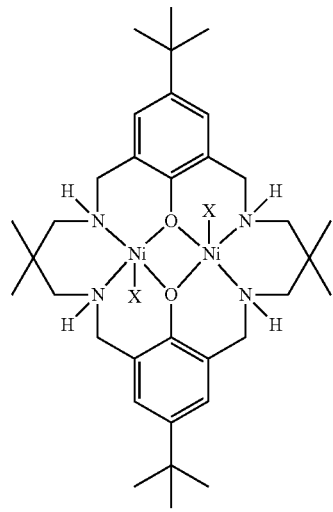
X = OAc
[L¹Ni₂(OAc)₂]
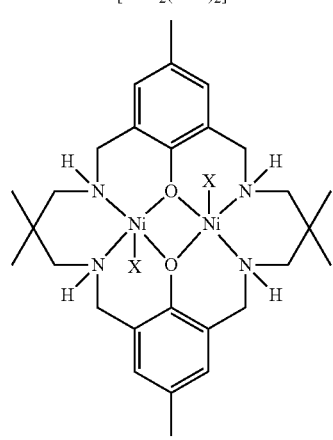
X = OAc
[L²Ni₂(OAc)₂]
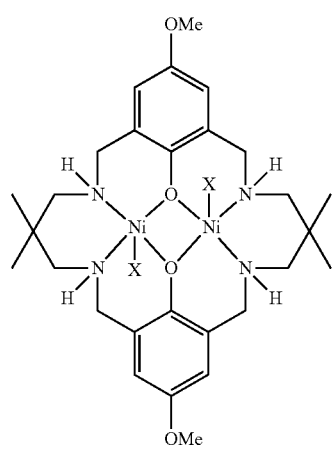
X = OAc
[L³Ni₂(OAc)₂]
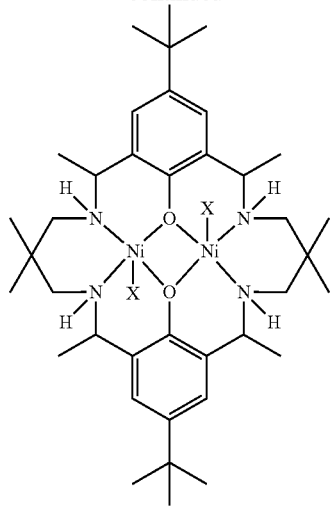
X = OAc
[L⁴Ni₂(OAc)₂]
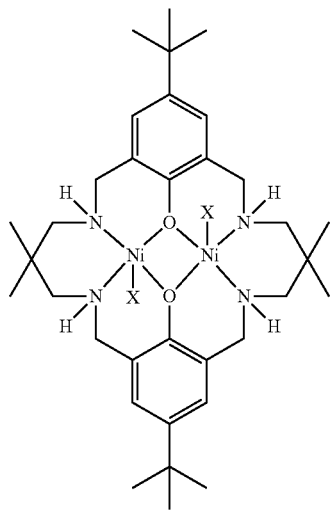
X = O₂CCF₃
[L¹Ni₂(O₂CCF₃)₂]
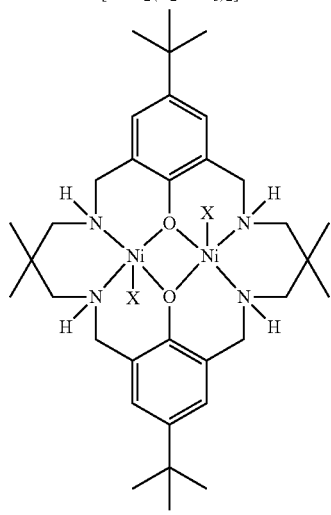
X = O₂C(CH₂)₃Cy
[L¹Ni₂(O₂C(CH₂)₃Cy)₂]

-continued

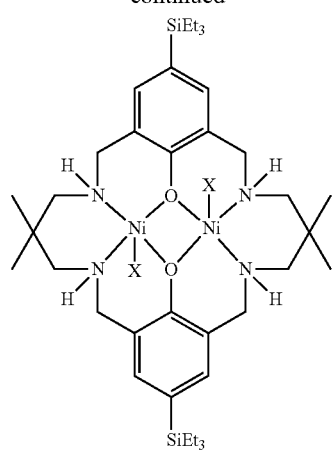

X = OAc
[L⁵Ni₂(OAc)₂]

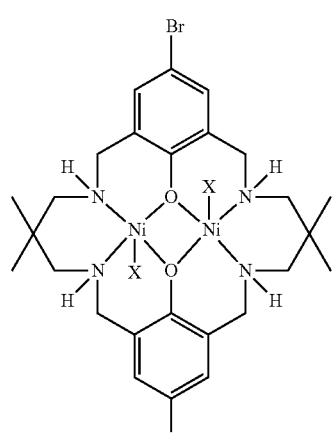

X = OAc
[L⁶Ni₂(OAc)₂]

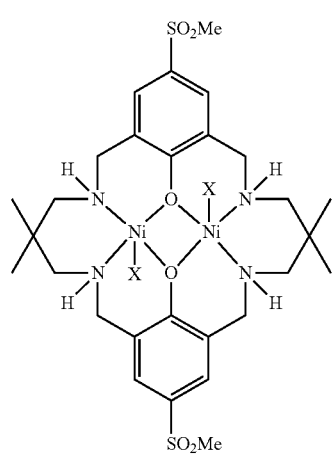

X = OAc
[L⁷Ni₂(OAc)₂]

-continued

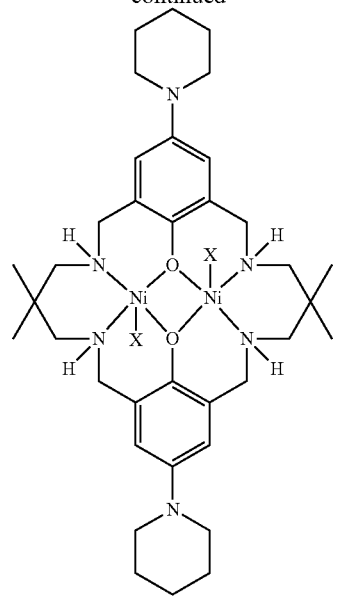

X = OAc
[L⁸Ni₂(OAc)₂]

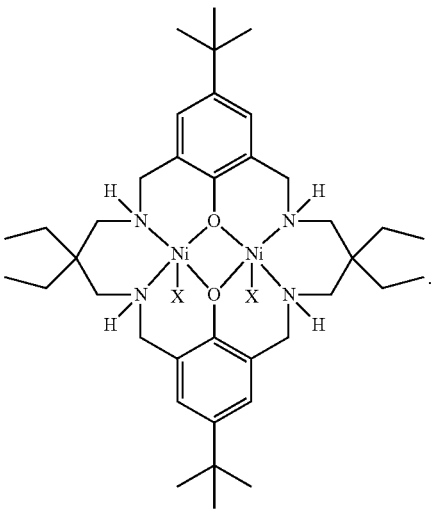

X = OAc
[L¹⁸Ni₂(OAc)₂]

49. A process for the reaction of:
  a. carbon dioxide with an epoxide;
  b. an epoxide and an anhydride; and/or
  c. a lactide and/or a lactone,
  in the presence of the catalyst of claim 1.

50. The process of claim 49, wherein the epoxide is ethylene oxide, butylene oxide, propylene oxide or cyclohexene oxide.

51. A catalyst of formula (I):

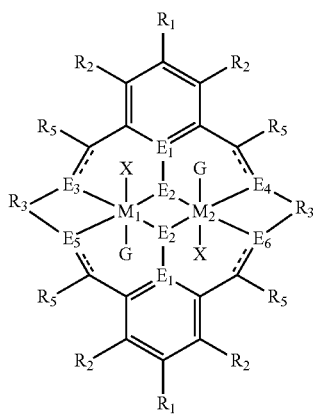

(I)

wherein:
M$_1$ and M$_2$ are independently selected from Zn(II), Cr(II), Co(II), Cu(II), Mn(II), Mg(II), Ni(II), Fe(II), Ti(II), V(II), Cr(III)-X, Mn(III)-X, Ni(III)-X, Fe(III)-X, Ca(II), Ge(II), Al(III)-X, Ti(III)-X, Ge(IV)-(X)$_2$ or Ti(IV)-(X)$_2$;

wherein at least one of M$_1$ or M$_2$ is selected from Ni(II) and Ni(III)-X;

R$_1$ is independently selected from halide, sulfoxide, silyl, and an optionally substituted alkyl, heteroaryl or alkoxy R$_2$ is independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

R$_3$ is independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic;

R$_5$ is independently selected from H, or optionally substituted aliphatic, heteroaliphatic, alicyclic, heteroalicyclic, aryl, heteroaryl, alkylheteroaryl or alkylaryl;

E$_1$ is C, E$_2$ is O, S or NH or E$_1$ is N and E$_2$ is O;

E3, E4, E5 and E6 are selected from N, NR$_4$, O and S, wherein when E3, E4, E5 or E6 are N, ----- is =====, and wherein when E3, E4, E5 or E6 are NR$_4$, O or S, ----- is ———;

R$_4$ is independently selected from hydrogen, or optionally substituted aliphatic, heteroaliphatic, alicyclic, heteroalicyclic, aryl, heteroaryl, alkylheteroaryl or alkylaryl;

X is independently selected from OC(O)R$^x$, OSO$_2$R$^x$, OSOR$^x$, OSO(R$^x$)$_2$, S(O)R$^x$, OR$^x$, phosphinate, halide, nitrate, hydroxyl, carbonate, amino, nitro, amido or optionally substituted aliphatic, heteroaliphatic, alicyclic, heteroalicyclic, aryl or heteroaryl;

R$_x$ is independently hydrogen, or optionally substituted aliphatic, haloaliphatic, heteroaliphatic, alicyclic, heteroalicyclic, aryl, alkylaryl or heteroaryl; and G is absent or independently selected from a neutral or anionic donor ligand which is a Lewis base.

52. The catalyst of claim 51 of the formula:

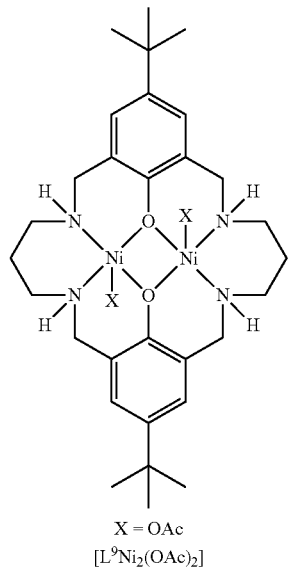

X = OAc
[L$^9$Ni$_2$(OAc)$_2$]

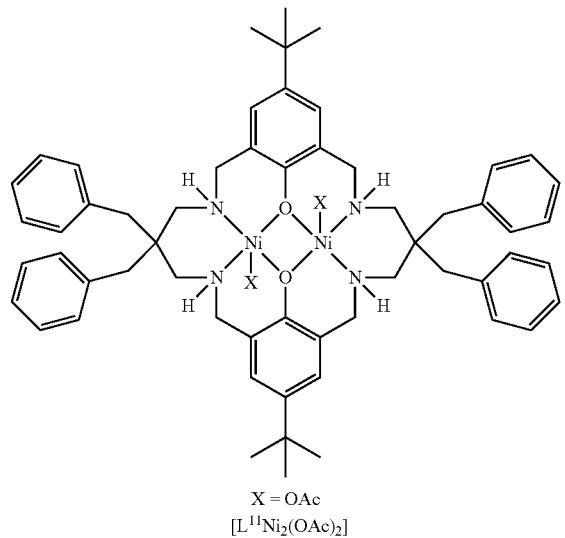

X = OAc
[L$^{11}$Ni$_2$(OAc)$_2$]

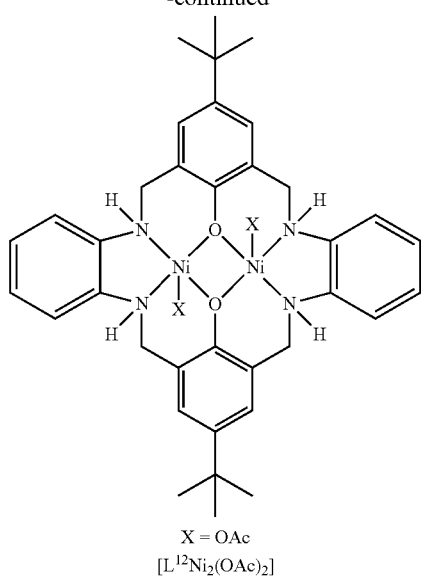
X = OAc
[L$^{12}$Ni$_2$(OAc)$_2$]
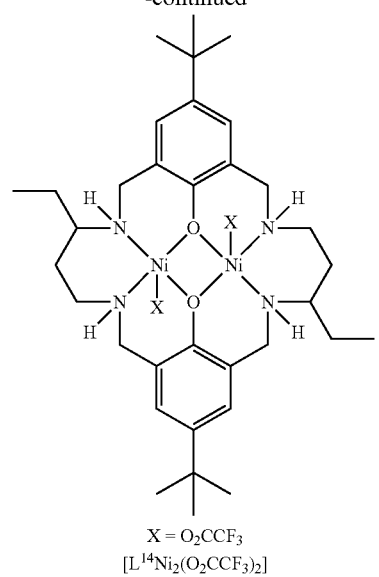
X = O$_2$CCF$_3$
[L$^{14}$Ni$_2$(O$_2$CCF$_3$)$_2$]
X = OAc
[L$^{13}$Ni$_2$(OAc)$_2$]
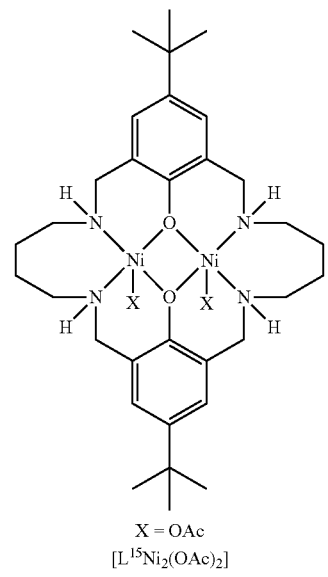
X = OAc
[L$^{15}$Ni$_2$(OAc)$_2$]
X = OAc
[L$^{14}$Ni$_2$(OAc)$_2$]
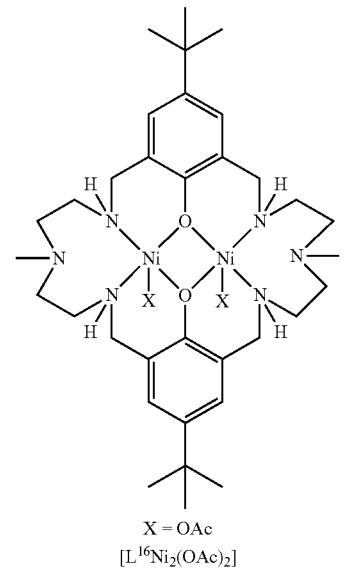
X = OAc
[L$^{16}$Ni$_2$(OAc)$_2$]

-continued
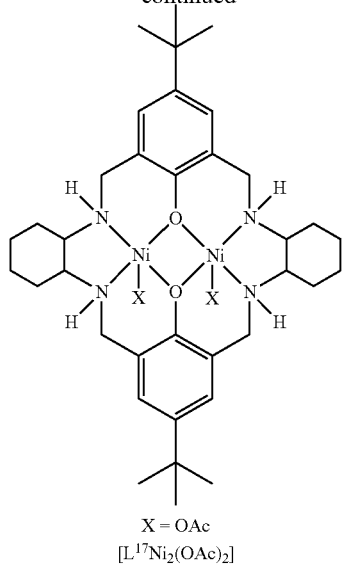
X = OAc
[L¹⁷Ni₂(OAc)₂]
53. A process for the reaction of:
a. carbon dioxide with an epoxide;
b. an epoxide and an anhydride; and/or
c. a lactide and/or a lactone,
in the presence of the catalyst of claim 51.
* * * * *

UNITED STATES PATENT AND TRADEMARK OFFICE
CERTIFICATE OF CORRECTION

PATENT NO. : 10,030,102 B2  
APPLICATION NO. : 15/327677  
DATED : July 24, 2018  
INVENTOR(S) : Colin Keyworth et al.

Page 1 of 1

It is certified that error appears in the above-identified patent and that said Letters Patent is hereby corrected as shown below:

In the Claims

Claim 1, Column 42, Line 26, after "Mn(III)-X" and before "Fe(III)-X" insert --Ni(III)-X--;

Claim 3, Column 42, Line 67, delete "Cu(II)" first occurrence;

Claim 3, Column 42, Line 67, before "Co(III)-X" add --Cr(II),--;

Claim 51, Column 51, Line 25, after "Cr(III)-X" and before "Mn(III)-X", add --CO(III)-X--;

Claim 51, Column 51, Line 26, after "Ti(III)-X" and before "Ge(IV)-(X)$_2$" add --V(III)-X;--.

Signed and Sealed this  
Twelfth Day of May, 2020

Andrei Iancu  
*Director of the United States Patent and Trademark Office*